US012260672B1

(12) United States Patent
Jung et al.

(10) Patent No.: US 12,260,672 B1
(45) Date of Patent: Mar. 25, 2025

(54) WEARABLE ELECTRONIC DEVICE FOR OBTAINING BIOMETRIC INFORMATION

(71) Applicant: Samsung Electronics Co., Ltd., Suwon-si (KR)

(72) Inventors: Hyunjun Jung, Suwon-si (KR); Hyoujoo Kwon, Suwon-si (KR); Hyuncheol Park, Suwon-si (KR); Soohan Yoo, Suwon-si (KR); Seungwon Lee, Suwon-si (KR); Seongwook Jo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 18/965,589

(22) Filed: Dec. 2, 2024

Related U.S. Application Data

(63) Continuation of application No. PCT/KR2024/013617, filed on Sep. 9, 2024.

(30) Foreign Application Priority Data

Sep. 21, 2023 (KR) .................. 10-2023-0126112
Nov. 7, 2023 (KR) .................. 10-2023-0152925

(51) Int. Cl.
 *G06V 40/13* (2022.01)
 *G06F 1/16* (2006.01)
 *H05K 1/18* (2006.01)
(52) U.S. Cl.
 CPC .......... *G06V 40/1318* (2022.01); *G06F 1/163* (2013.01); *G06F 1/1635* (2013.01); *H05K 1/189* (2013.01)
(58) Field of Classification Search
 CPC ... G06V 40/1318; G06F 1/163; G06F 1/1635; H05K 1/189
 (Continued)

(56) References Cited

U.S. PATENT DOCUMENTS 5,964,701 A * 10/1999 Asada .................. A61B 5/002
 128/903
11,278,220 B2 * 3/2022 Tucker ............... A61B 5/14552
 (Continued)

FOREIGN PATENT DOCUMENTS

CN 109426305 A * 3/2019 ........... A61B 5/0059
CN 115469738 A * 12/2022 ......... A61B 5/14552
 (Continued)

OTHER PUBLICATIONS

International Search Report with Written Opinion and English translation dated Dec. 18, 2024; International Appln. No. PCT/KR2024/013617.

*Primary Examiner* — Mahendra R Patel
(74) *Attorney, Agent, or Firm* — Jefferson IP Law, LLP

(57) ABSTRACT

A ring-type wearable electronic device is provided. The ring-type wearable electronic device includes a ring-shape housing including a first housing portion and a second housing portion coupled to the first housing portion, wherein the second housing portion is configured to contact a finger of a user wearing the ring-type wearable electronic device, a first light source including a plurality of light emitters disposed in the ring-shape housing, and configured to emit light of red wavelength and infrared wavelength bands towards the finger, a first sensor disposed in the ring-shape housing, and configured to receive light emitted by the first light source, a second sensor disposed in the ring-shape housing, and configured to receive light emitted by the first light source, wherein the first sensor is positioned farther from the first light source than the second sensor is positioned from the first light source, a flexible printed circuit board (FPCB) disposed in the ring-shape housing, wherein the first light source, the first sensor, and the second sensor are disposed on the FPCB at least partially bent correspond- (Continued)

ing to the ring-shape housing, at least one processor including a processing circuitry, and memory storing instructions, wherein the instructions, when executed by the at least one processor individually or collectively, cause the ring-type wearable electronic device to: emit, by the first light source at a first time, first light of red wavelength and infrared wavelength bands, the first light being configured to reach the first sensor through the finger, based on the first light emitted by the first light source at the first time, obtain first information corresponding to part of the first light that is received by the first sensor via the finger, emit, by the first light source at a second time different from the first time, second light of red wavelength and infrared wavelength bands, the second light being configured to reach the second sensor through the finger, based on the second light emitted by the first light source at the second time, obtain second information corresponding to part of the second light that is received by the second sensor via the finger, and acquire an oxygen saturation information of the user based on at least one of the first information or the second information.

27 Claims, 20 Drawing Sheets

(58) Field of Classification Search
USPC .......................................................... 382/124
See application file for complete search history.

(56) References Cited

U.S. PATENT DOCUMENTS

| | | | |
|---|---|---|---|
| 11,911,181 B1* | 2/2024 | Huttunen | A61B 5/683 |
| 2015/0133753 A1* | 5/2015 | Karp | A61B 5/0002 |
| | | | 600/323 |
| 2016/0198962 A1 | 7/2016 | Park et al. | |
| 2017/0360316 A1* | 12/2017 | Gu | A61B 5/14552 |
| 2018/0132738 A1 | 5/2018 | Choi et al. | |
| 2019/0167199 A1* | 6/2019 | Nam | A61B 5/7405 |
| 2020/0000345 A1* | 1/2020 | Connor | A61B 5/14532 |
| 2020/0034596 A1* | 1/2020 | He | G06V 40/1324 |
| 2020/0233452 A1 | 7/2020 | Von Badinski et al. | |
| 2020/0275871 A1* | 9/2020 | Al-Ali | A61B 5/14546 |
| 2020/0329985 A1* | 10/2020 | Wong | A61B 5/6833 |
| 2020/0342197 A1* | 10/2020 | Du | G06V 40/1318 |
| 2021/0037932 A1* | 2/2021 | Min | A61B 5/0006 |
| 2021/0093237 A1* | 4/2021 | Venugopal | H01L 31/16 |
| 2021/0169345 A1* | 6/2021 | Wasson | G01N 21/3577 |
| 2022/0057832 A1* | 2/2022 | von Badinski | A61B 5/1118 |
| 2022/0160239 A1 | 5/2022 | Nam et al. | |
| 2022/0340042 A1* | 10/2022 | Schreiber | B60L 58/16 |
| 2022/0415476 A1* | 12/2022 | Connor | G06V 20/20 |
| 2023/0079736 A1* | 3/2023 | Mäkinen | G01N 21/4133 |
| | | | 600/300 |
| 2023/0081794 A1* | 3/2023 | Mäkinen | G01N 21/4133 |
| | | | 356/614 |
| 2023/0113714 A1* | 4/2023 | Vallius | A61B 5/0816 |
| | | | 398/25 |
| 2023/0255524 A1* | 8/2023 | Ohara | A61B 5/1171 |
| | | | 600/323 |
| 2023/0380692 A1* | 11/2023 | Huttunen | G06F 1/163 |
| 2023/0386245 A1* | 11/2023 | Tada | G06V 10/955 |
| 2024/0000328 A1* | 1/2024 | Kangas | A61B 5/02438 |
| 2024/0053522 A1* | 2/2024 | Acharya | G06V 40/13 |
| 2024/0090835 A1* | 3/2024 | Watanabe | A61B 5/6826 |
| 2024/0219237 A1* | 7/2024 | Mäkinen | G01J 3/50 |
| 2024/0385649 A1* | 11/2024 | Tiensuu | G06F 1/1635 |

FOREIGN PATENT DOCUMENTS

| | | | | |
|---|---|---|---|---|
| EP | 2505141 A1 * | 10/2012 | | A61B 1/0638 |
| JP | 2000-342547 A | 12/2000 | | |
| JP | 2019-166149 A | 10/2019 | | |
| JP | 2022-071208 A | 5/2022 | | |
| KR | 10-2000-0052757 A | 8/2000 | | |
| KR | 10-2016-0086710 A | 7/2016 | | |
| KR | 10-2016-0127641 A | 11/2016 | | |
| KR | 10-2017-0091346 A | 8/2017 | | |
| KR | 10-2019-0065089 A | 6/2019 | | |
| KR | 10-2022-0060783 A | 5/2022 | | |
| KR | 10-2022-0070792 A | 5/2022 | | |
| KR | 10-2022-0091141 A | 6/2022 | | |
| KR | 10-2023-0077932 A | 6/2023 | | |
| WO | WO-2015126095 A1 * | 8/2015 | | A61B 5/0022 |
| WO | 2015/153803 A1 | 10/2015 | | |
| WO | WO-2022139233 A1 * | 6/2022 | | A61B 5/0059 |
| WO | WO-2023043194 A1 * | 3/2023 | | A61B 5/00 |
| WO | WO-2024009790 A1 * | 1/2024 | | |
| WO | WO-2024034431 A1 * | 2/2024 | | |

\* cited by examiner

WEARABLE ELECTRONIC DEVICE FOR OBTAINING BIOMETRIC INFORMATION

CROSS-REFERENCE TO RELATED APPLICATION(S)

This application is a continuation application, claiming priority under § 365 (c), of an International application No. PCT/KR2024/013617, filed on Sep. 9, 2024, which is based on and claims the benefit of a Korean patent application number 10-2023-0126112, filed on Sep. 21, 2023, in the Korean Intellectual Property Office, and of a Korean application number 10-2023-0152925, filed on Nov. 7, 2023, in the Korean Intellectual Property Office, the disclosure of each of which is incorporated by reference herein in its entirety.

BACKGROUND

1. Field

The disclosure relates to a wearable electronic device. More particularly, the disclosure relates to a wearable electronic device for obtaining biometric information.

2. Description of Related Art

Recent electronic devices come in various form factors for user convenience purposes and in reduced size for easy carrying. For example, the electronic device may be provided in the form of a ring that may be worn on the user's finger. More interest is being paid to health, and so is technology capable of checking up the health condition.

Accordingly, electronic devices may include a sensor for measuring the user's biometric information and have been developed to measure and utilize various biometric signals using the sensor and provide various services for the user's health care or check on the user's health condition through measurement of various biometric signals.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide a wearable electronic device for obtaining biometric information.

Additional aspects will be set forth in part in the description which follows and, in part, will be apparent from the description, or may be learned by practice of the presented embodiments.

In accordance with an aspect of the disclosure, a ring-type wearable electronic device is provided. The ring-type wearable electronic device includes a ring-shape housing including a first housing portion and a second housing portion coupled to the first housing portion, wherein the second housing portion is configured to contact a finger of a user wearing the ring-type wearable electronic device, a first light source including a plurality of light emitters disposed in the ring-shape housing, and configured to emit light of red wavelength and infrared wavelength bands towards the finger, a first sensor disposed in the ring-shape housing, and configured to receive light emitted by the first light source, a second sensor disposed in the ring-shape housing, and configured to receive light emitted by the first light source, wherein the first sensor is positioned farther from the first light source than the second sensor is positioned from the first light source, a flexible printed circuit board (FPCB) disposed in the ring-shape housing, wherein the first light source, the first sensor, and the second sensor are disposed on the FPCB at least partially bent corresponding to the ring-shape housing, at least one processor including a processing circuitry, and memory storing instructions, wherein the instructions, when executed by the at least one processor individually or collectively, cause the ring-type wearable electronic device to: emit, by the first light source at a first time, first light of red wavelength and infrared wavelength bands, the first light being configured to reach the first sensor through the finger, based on the first light emitted by the first light source at the first time, obtain first information corresponding to part of the first light that is received by the first sensor via the finger, emit, by the first light source at a second time different from the first time, second light of red wavelength and infrared wavelength bands, the second light being configured to reach the second sensor through the finger, based on the second light emitted by the first light source at the second time, obtain second information corresponding to part of the second light that is received by the second sensor via the finger, and acquire an oxygen saturation information of the user based on at least one of the first information or the second information.

According to an embodiment of the disclosure, a method performed by a wearable electronic device includes emitting, by a first light source at a first time, first light of red wavelength and infrared wavelength bands, the first light being configured to reach a first sensor through a finger, based on the first light emitted by the first light source at the first time, obtaining first information corresponding to part of the first light that is received by the first sensor via the finger, emitting, by the first light source at a second time different from the first time, second light of red wavelength and infrared wavelength bands, the second light being configured to reach a second sensor through the finger, based on the second light emitted by the first light source at the second time, obtaining second information corresponding to part of the second light that is received by the second sensor via the finger, and acquiring an oxygen saturation information of a user based on at least one of the first information or the second information.

In accordance with an aspect of the disclosure, one or more non-transitory computer-readable storage media storing one or more computer-executable instructions that, when executed by one or more processors of an electronic device individually or collectively, cause a ring-type wearable electronic device to perform operations are provided. The operations include emitting, by a first light source at a first time, first light of red wavelength and infrared wavelength bands, the first light being configured to reach a first sensor through a finger, based on the first light emitted by the first light source at the first time, obtaining first information corresponding to part of the first light that is received by the first sensor via the finger, emitting, by the first light source at a second time different from the first time, second light of red wavelength and infrared wavelength bands, the second light being configured to reach a second sensor through the finger, based on the second light emitted by the first light source at the second time, obtaining second information corresponding to part of the second light that is received by the second sensor via the finger, and acquiring an oxygen saturation information of a user based on at least one of the first information or the second information.

In accordance with an aspect of the disclosure, a ring-type wearable electronic device is provided. The ring-type wearable electronic device includes a ring-shape housing including a first housing portion and a second housing portion coupled to the first housing portion, wherein the second housing portion is configured to contact a finger of a user wearing the ring-type wearable electronic device, a first light source including a plurality of light emitters disposed in an ring-shape housing, and configured to emit light of red wavelength and infrared wavelength bands, a first sensor disposed in the ring-shape housing, and configured to receive light emitted by the first light source, a second sensor disposed in the ring-shape housing, and configured to receive light emitted by the first light source, wherein the first sensor is positioned farther from the first light source than the second sensor is positioned from the first light source, a second light source disposed in the ring-shape housing and between the first sensor and the second sensor along the ring-shape housing, and configured to emit light of red wavelength and infrared wavelength bands towards the finger, wherein the second light source is positioned closer to the first sensor than the second sensor is positioned to the second sensor, at least one processor including a processing circuitry, and memory storing instructions, wherein the instructions, when executed by the at least one processor individually or collectively, cause the ring-type wearable electronic device to: emit, by the first light source, first light of red wavelength and infrared wavelength bands, the first light being configured to reach the first sensor through the finger, based on the first light emitted by the first light source, obtain first information corresponding to part of the first light that is received by the first sensor via the finger, emit, by the first light source, second light of red wavelength and infrared wavelength bands, the second light being configured to reach the second sensor through the finger, based on the second light emitted by the first light source, obtain second information corresponding to part of the second light that is received by the second sensor via the finger, and acquire an oxygen saturation of the user based on at least one of the first information or the second information.

According to an embodiment of the disclosure, a method performed by a wearable electronic device includes emitting, by a first light source, first light of red wavelength and infrared wavelength bands, the first light being configured to reach a first sensor through a finger, based on the first light emitted by the first light source, obtaining first information corresponding to part of the first light that is received by the first sensor via the finger, emitting, by the first light source, second light of red wavelength and infrared wavelength bands, the second light being configured to reach a second sensor through the finger, based on the second light emitted by the first light source, obtaining second information corresponding to part of the second light that is received by the second sensor via the finger, and acquiring an oxygen saturation of a user based on at least one of the first information or the second information.

In accordance with an aspect of the disclosure, one or more non-transitory computer-readable storage media storing one or more computer-executable instructions that, when executed by one or more processors of an electronic device individually or collectively, cause a ring-type wearable electronic device to perform operations are provided. The operations include emitting, by a first light source, first light of red wavelength and infrared wavelength bands, the first light being configured to reach a first sensor through a finger, based on the first light emitted by the first light source, obtaining first information corresponding to part of the first light that is received by the first sensor via the finger, emitting, by the first light source, second light of red wavelength and infrared wavelength bands, the second light being configured to reach a second sensor through the finger, based on the second light emitted by the first light source, obtaining second information corresponding to part of the second light that is received by the second sensor via the finger, and acquiring an oxygen saturation of a user based on at least one of the first information or the second information.

In accordance with an aspect of the disclosure, a ring-type wearable electronic device is provided. The ring-type wearable electronic device includes a ring-shape housing including a first housing portion and a second housing portion coupled to the first housing portion, wherein the second housing portion is configured to contact a finger of a user wearing the ring-type wearable electronic device, a first light source including a plurality of light emitters disposed in the ring-shape housing, and configured to emit light of red wavelength and infrared wavelength bands towards the finger, a first sensor disposed in the ring-shape housing, and configured to receive light emitted by the first light source, a second sensor disposed in the ring-shape housing, and configured to receive light emitted by the first light source, wherein the first sensor is positioned farther from the first light source than the second sensor is positioned from the first light source, at least one processor including a processing circuitry, and memory storing instructions, wherein the instructions, when executed by the at least one processor individually or collectively, cause the ring-type wearable electronic device to: emit, by the first light source, first light, having a first intensity, of red wavelength and infrared wavelength bands, the first light being configured to reach the first sensor through the finger, based on the first light emitted by the first light source, obtain first information corresponding to part of the first light that is received by the first sensor via the finger, emit, by the first light source, second light, having a second intensity lower than the first intensity, of red wavelength and infrared wavelength bands, the second light being configured to reach the second sensor through the finger, based on the second light emitted by the first light source, obtain second information corresponding to part of the second light that is received by the second sensor via the finger, and acquire an oxygen saturation information of the user based on at least one of the first information or the second information.

According to an embodiment of the disclosure, a method performed by a wearable electronic device includes emitting, by a first light source, first light, having a first intensity, of red wavelength and infrared wavelength bands, the first light being configured to reach a first sensor through a finger, based on the first light emitted by the first light source, obtaining first information corresponding to part of the first light that is received by the first sensor via the finger, emitting, by the first light source, second light, having a second intensity lower than the first intensity, of red wavelength and infrared wavelength bands, the second light being configured to reach a second sensor through the finger, based on the second light emitted by the first light source, obtaining second information corresponding to part of the second light that is received by the second sensor via the finger, and acquiring an oxygen saturation information of a user based on at least one of the first information or the second information.

In accordance with an aspect of the disclosure, one or more non-transitory computer-readable storage media storing one or more computer-executable instructions that, when executed by one or more processors of an electronic device individually or collectively, cause a ring-type wearable electronic device to perform operations are provided. The operations include emitting, by a first light source, first light, having a first intensity, of red wavelength and infrared wavelength bands, the first light being configured to reach a first sensor through a finger, based on the first light emitted by the first light source, obtaining first information corresponding to part of the first light that is received by the first sensor via the finger, emitting, by the first light source, second light, having a second intensity lower than the first intensity, of red wavelength and infrared wavelength bands, the second light being configured to reach a second sensor through the finger, based on the second light emitted by the first light source, obtaining second information corresponding to part of the second light that is received by the second sensor via the finger, and acquiring an oxygen saturation information of a user based on at least one of the first information or the second information.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

The same reference numerals are used to represent the same elements throughout the drawings.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

It should be appreciated that the blocks in each flowchart and combinations of the flowcharts may be performed by one or more computer programs which include instructions. The entirety of the one or more computer programs may be stored in a single memory device or the one or more computer programs may be divided with different portions stored in different multiple memory devices.

Any of the functions or operations described herein can be processed by one processor or a combination of processors. The one processor or the combination of processors is circuitry performing processing and includes circuitry like an application processor (AP, e.g. a central processing unit (CPU)), a communication processor (CP, e.g., a modem), a graphics processing unit (GPU), a neural processing unit (NPU) (e.g., an artificial intelligence (AI) chip), a Wi-Fi chip, a Bluetooth® chip, a global positioning system (GPS)

chip, a near field communication (NFC) chip, connectivity chips, a sensor controller, a touch controller, a finger-print sensor controller, a display driver integrated circuit (IC), an audio CODEC chip, a universal serial bus (USB) controller, a camera controller, an image processing IC, a microprocessor unit (MPU), a system on chip (SoC), an IC, or the like.

Figure 1:
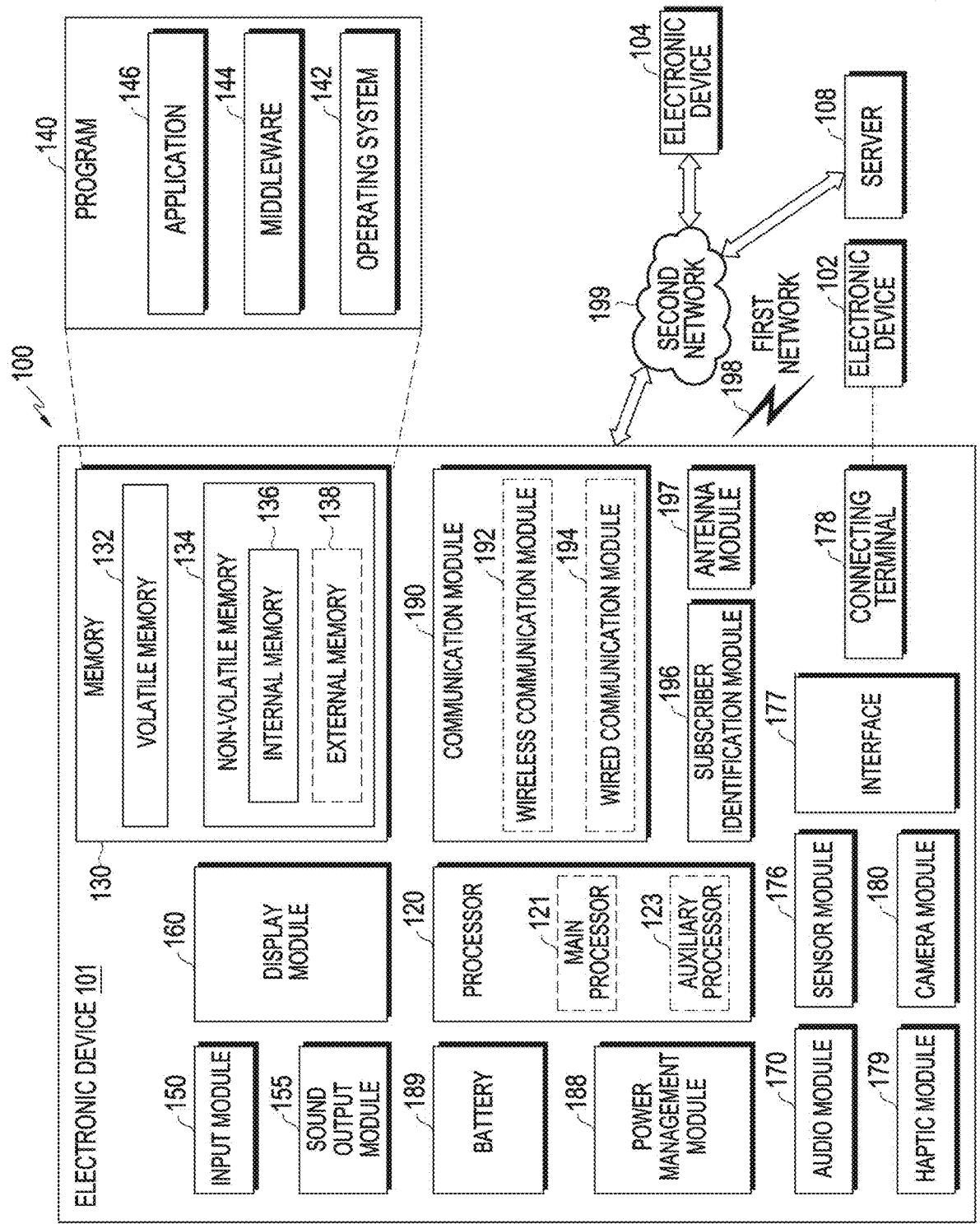
FIG. 1 is a view illustrating an electronic device in a network environment according to an embodiment of the disclosure.

FIG. 1 is a block diagram illustrating an electronic device 101 in a network environment 100 according to an embodiment of the disclosure.

Referring to FIG. 1, the electronic device 101 in the network environment 100 may communicate with at least one of an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In an embodiment, at least one (e.g., the connecting terminal 178) of the components may be omitted from the electronic device 101, or one or more other components may be added in the electronic device 101. According to an embodiment, some (e.g., the sensor module 176, the camera module 180, or the antenna module 197) of the components may be integrated into a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be configured to use lower power than the main processor 121 or to be specified for a designated function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. The artificial intelligence model may be generated via machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by other component (e.g., the processor 120) of the electronic device 101, from the outside (e.g., a user) of the electronic device 101. The input module 150 may include, for example, a microphone, a mouse, a keyboard, keys (e.g., buttons), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor configured to detect a touch, or a pressure sensor configured to measure the intensity of a force generated by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an accelerometer, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, an HDMI connector, a USB connector, an SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device 104 via a first network 198 (e.g., a short-range communication network, such as Bluetooth™ wireless-fidelity (Wi-Fi) direct, or infrared data association (IrDA)) or a second network 199 (e.g., a long-range communication network, such as a legacy cellular network, a fifth-generation (5G) network, a next-generation communication network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 192 may identify or authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a fourth-generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the millimeter wave (mmWave) band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device). According to an embodiment, the antenna module 197 may include one antenna including a radiator formed of a conductor or conductive pattern formed on a substrate (e.g., a printed circuit board (PCB)). According to an embodiment, the antenna module 197 may include a plurality of antennas (e.g., an antenna array). In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment, other parts (e.g., radio frequency integrated circuit (RFIC)) than the radiator may be further formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. The external electronic devices 102 or 104 each may be a device of the same or a different type from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an Internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or health-care) based on 5G communication technology or IoT-related technology.

Figure 2:
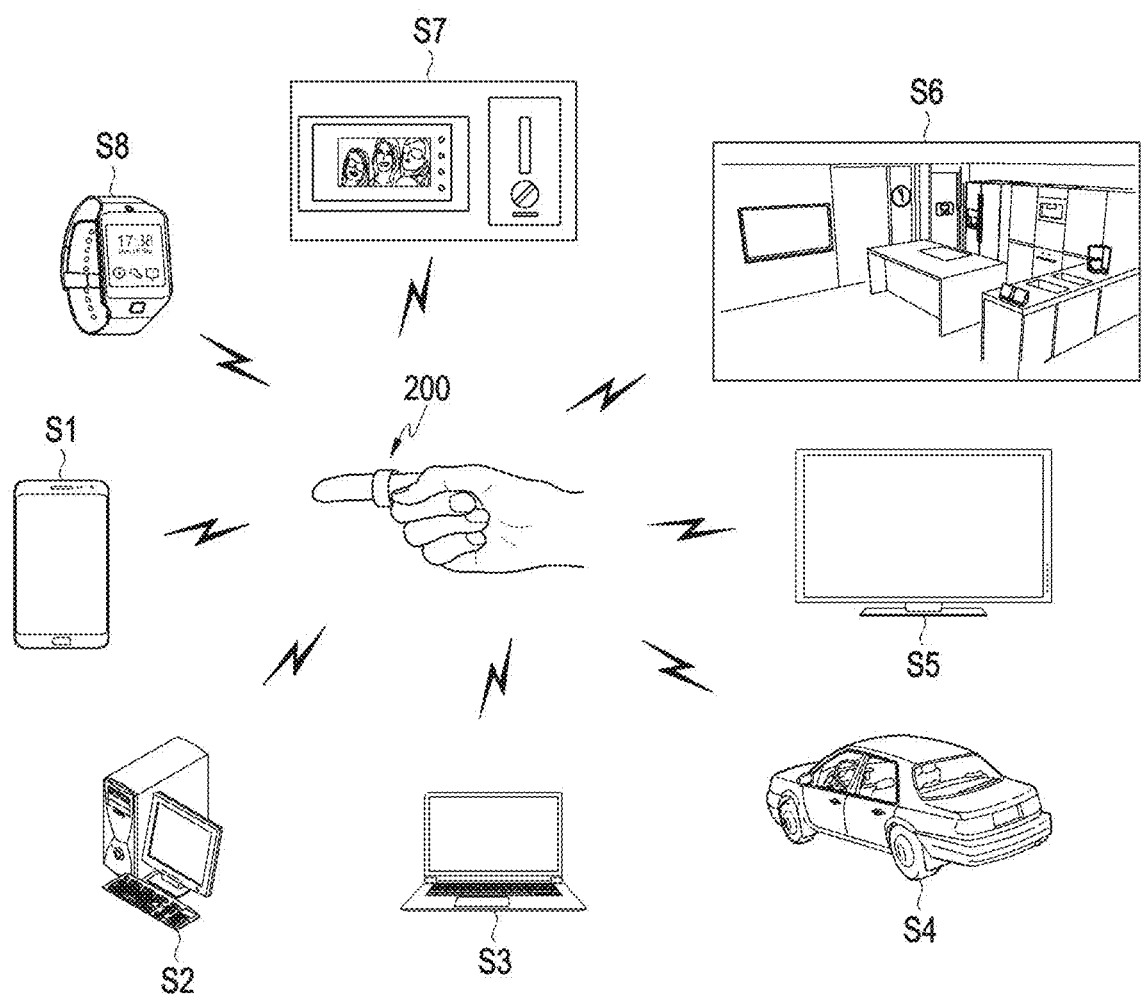
FIG. 2 is a view illustrating usage examples of a wearable electronic device according to an embodiment of the disclosure.

FIG. 2 is a view illustrating usage examples of a wearable electronic device according to an embodiment of the disclosure.

The embodiment of FIG. 2 may be combined with the embodiment of FIG. 1 or the embodiments of FIGS. 3 to 8, 9A to 9D, and 10 to 19.

Referring to FIG. 2, a wearable electronic device 200 (e.g., the electronic device 101 of FIG. 1) may be configured to be wearable on the user's body. For example, the wearable electronic device 200 may be implemented as a wearable electronic device wearable on the user's finger. For example, the wearable electronic device 200 may be provided in the form of a ring that may be worn on the user's finger. The wearable electronic device 200 may be defined and/or referred to as a smart ring.

According to an embodiment, the wearable electronic device 200 may perform wireless communication with another electronic device (e.g., the electronic device 102 or 104 of FIG. 1) through a wireless communication network (e.g., the first network 198 or the second network 199 of FIG. 1). For example, the wearable electronic device 200 may perform wireless communication with another electronic device such as a smart phone S1, desktop/laptop computers S2 and S3, a car S4, a smart television (TV) S5, indoor smart home devices S6, a tablet personal computer (PC) S7, or a smart watch S8. Wireless communication between the wearable electronic device 200 and another electronic device may be implemented as wireless communication via a short-range communication network (e.g., the first network 198 of FIG. 1) or a long-range communication network (e.g., the second network 199 of FIG. 1). For example, if a Bluetooth communication link is established between the wearable electronic device 200 and the electronic device to which the user wants to access, a message may be transferred between the two electronic devices, and the wearable electronic device 200 worn by the user may generate a command corresponding to each specific motion/gesture of the user's finger and transfer the command to the other electronic device. Motion sensors (e.g., the sensor module 176 of FIG. 1) of an accelerometer, a gyroscope, or an electronic compass may be disposed in the wearable electronic device 200 to detect a finger motion/gesture of the user. If the message is received from the other electronic device to the wearable electronic device 200, the wearable electronic device 200 may notify the user of the message reception using sound, vibration, a display screen, or lighting (e.g., a light emitting diode or a xenon lamp). To that end, the wearable electronic device 200 may include a sound module (e.g., the sound output module 155 or the audio module 170 of FIG. 1), a haptic module (e.g., the haptic module 179 of FIG. 1), or a display module (e.g., the display module 160 of FIG. 1). According to an embodiment, at least one of an acoustic module, a haptic module, or a display module may be omitted from the wearable electronic device 200, or one or more other components may be output from the wearable electronic device 200. Further, the wearable electronic device 200 may acquire biometric information (e.g., oxygen saturation) of the user and provide the biometric information to the other electronic device.

Figure 3:
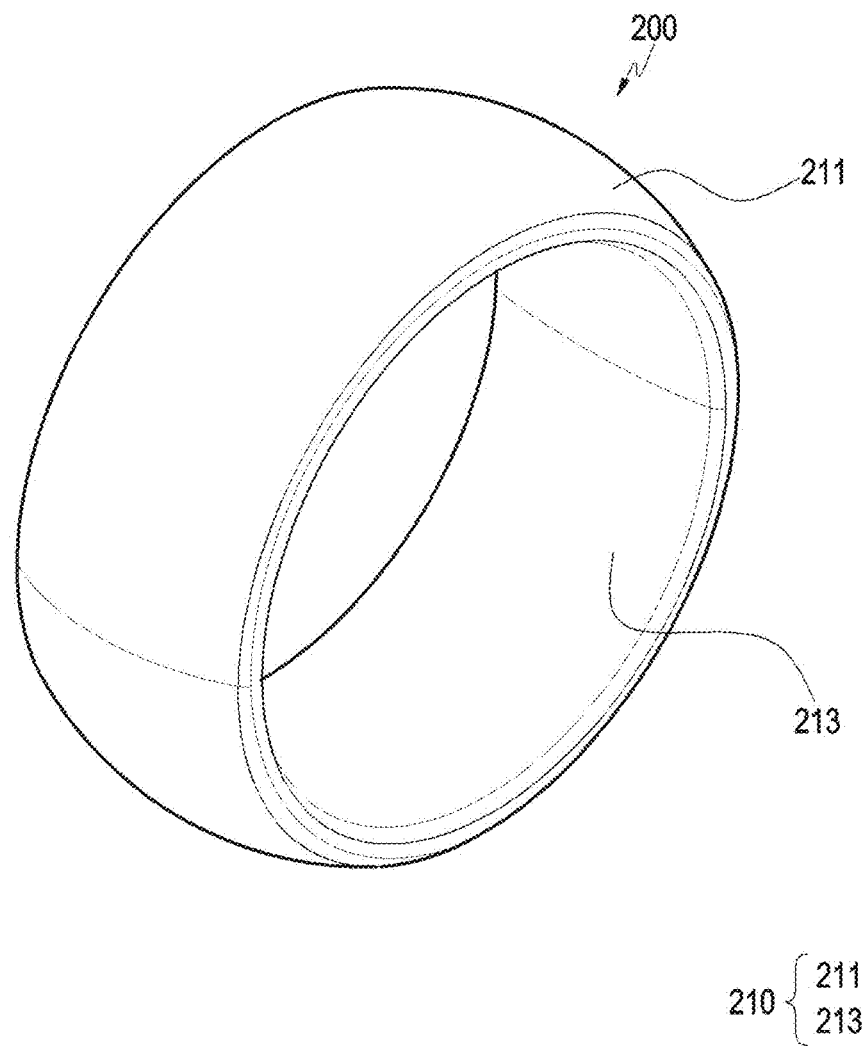
FIG. 3 is a perspective view illustrating a wearable electronic device according to an embodiment of the disclosure.

FIG. 3 is a perspective view illustrating a wearable electronic device according to an embodiment of the disclosure.

Figure 4:
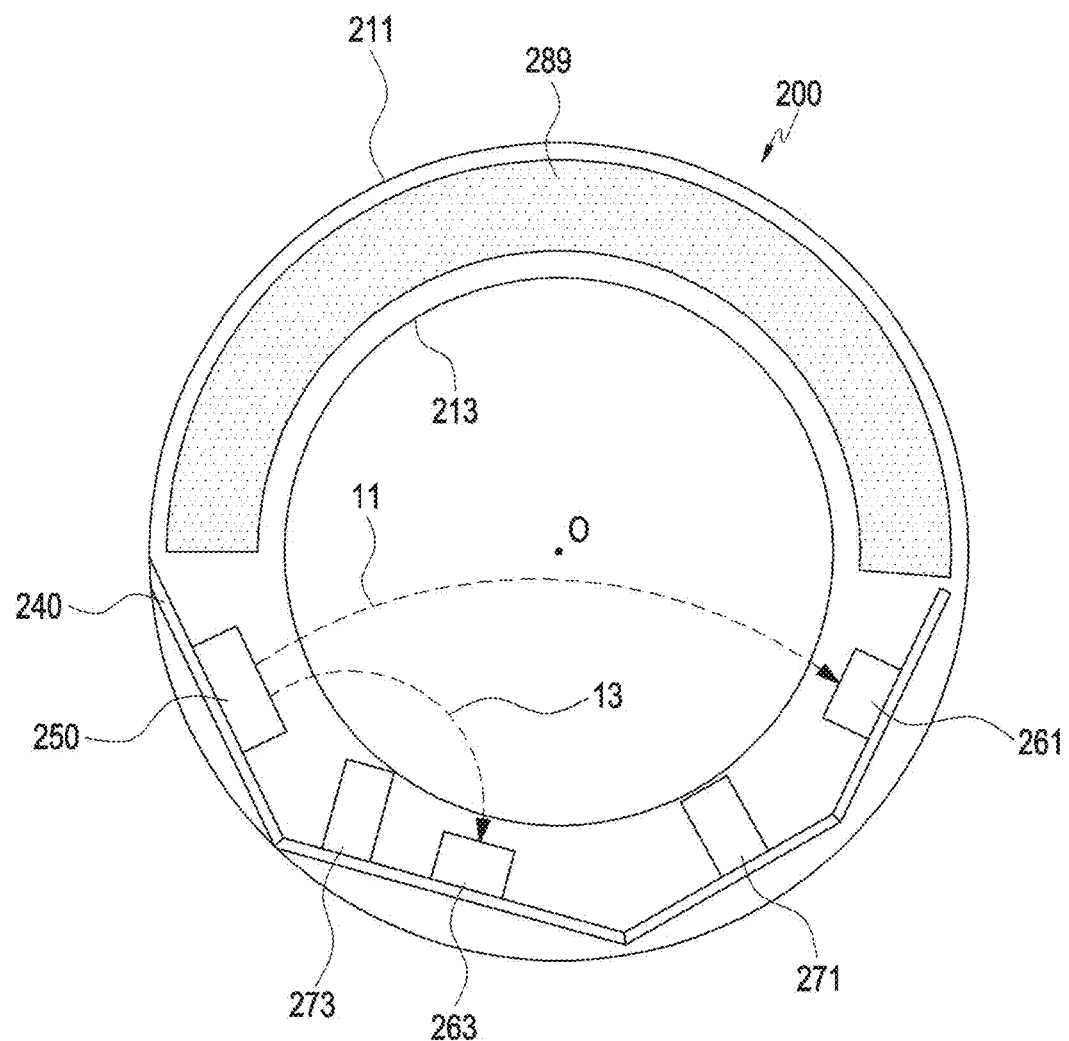
FIG. 4 is a cross-sectional view illustrating a wearable electronic device according to an embodiment of the disclosure.

FIG. 4 is a cross-sectional view illustrating a wearable electronic device according to an embodiment of the disclosure.

The embodiments of FIGS. 3 and 4 may be combined with the embodiments of FIGS. 1 and 2 or the embodiments of FIGS. 5 to 8, 9A to 9D, and 10 to 19.

The configuration of the wearable electronic device 200 of FIGS. 3 and 4 may be identical in whole or part to the configuration of the electronic device 101 of FIG. 1 or the configuration of the wearable electronic device 200 of FIG. 2.

Referring to FIGS. 3 and 4, the wearable electronic device 200 may include a housing 210. The housing 210 may form the overall appearance of the wearable electronic device 200.

According to an embodiment, the housing 210 may have a ring shape. The housing 210 may include an opening configured to accommodate the user's finger. For example, the opening may be defined as a hole formed in the housing 210.

According to an embodiment, the housing 210 may include an external housing portion 211 or an internal housing portion 213. The internal housing portion 213 may be coupled to the external housing portion 211. According to an embodiment, the external housing portion 211 and the internal housing portion 213 may be separately manufactured and assembled, or may be integrally formed.

According to an embodiment, the external housing portion 211 may include a material capable of withstanding external shocks and/or scratches and implementing design features. For example, the external housing portion 211 may include at least one of titanium, stainless steel, or ceramic. The external housing portion 211 may be colored or coated to implement a design.

According to an embodiment, the internal housing portion 213 may be a portion that touches the user's finger when the user wears the wearable electronic device 200. The internal housing portion 213 may be formed of a material such as a molding material, transparent plastic, or glass for sensing. For example, the internal housing portion 213 may be configured to be at least partially transparent. For example, the internal housing portion 213 may include a material capable of transmitting light for measuring biometric information. At least a portion of the internal housing portion 213 may be formed of a material substantially the same as or similar to that of the external housing portion 211. Further, at least a portion of the internal housing portion 213 may include a metal material for measuring biometric information.

According to an embodiment, the external housing portion 211 and the internal housing portion 213 may be coupled to provide an inner space of the housing 210. Various electrical/electronic components of the wearable electronic device 200 may be disposed and/or mounted in the inner space of the housing 210. For example, the housing 210 may accommodate various electrical/electronic components.

According to an embodiment, the wearable electronic device 200 may include a circuit board 240, at least one light emitter 250, at least one sensor 260, at least one blocking member 270, or a battery 289 (e.g., the battery 189 of FIG. 1).

According to an embodiment, the circuit board 240 may be disposed in the inner space of the housing 210. The circuit board 240 may include at least one of a printed circuit board (PCB), a flexible printed circuit board (FPCB), or a rigid-flexible PCB (RF-PCB).

According to an embodiment, various electrical/electronic components may be disposed and/or mounted on the circuit board 240. For example, a processor (e.g., the processor 120 of FIG. 1), memory (e.g., the memory 130 of FIG. 1), a communication module (e.g., the communication module 190 of FIG. 1), or a sensor module (e.g., the sensor module 176 of FIG. 1, the at least one light emitter 250 of FIG. 4, or the at least one sensor 260) may be mounted on the circuit board 240.

According to an embodiment, the circuit board 240 may include a plurality of printed circuit boards. For example, the plurality of printed circuit boards may be disposed according to the shape of the inner space of the housing 210 and may be electrically connected to each other. The circuit board 240 may include a flexible printed circuit board (FPCB). For example, the flexible printed circuit board may be at least partially bent according to the shape of the inner space of the housing 210.

According to an embodiment, the battery 289 is a device for supplying power to a component of the wearable electronic device 200 and may include a primary cell which is not rechargeable, a secondary cell which is rechargeable, or a fuel cell. The battery 289 may be integrally disposed inside the wearable electronic device 200 or may be detachably disposed from the wearable electronic device 200. According to an embodiment, the battery 289 may be formed of a single embedded battery or may include a plurality of removable batteries. The battery 289 may include a battery pack that is bent according to the shape of the inner space of the housing 210. The battery 289 may include a plurality of non-bendable battery packs of the housing 210. The battery 289 may include a battery pack that is bent and a plurality of non-bendable battery packs.

According to an embodiment, the wearable electronic device 200 may include a power management module (e.g., the power management module 188 of FIG. 1) disposed on the circuit board 240.

According to an embodiment, the wearable electronic device 200 may include a sensor for obtaining (or measuring) at least one piece of biometric information. For example, the at least one piece of biometric information may include at least one piece of information about the user's oxygen saturation or information about the user's heart rate. For example, the sensor may include a photoplethysmography (PPG) sensor for measuring oxygen saturation or heart rate.

According to an embodiment, the PPG sensor may include a light source (e.g., at least one light emitter 250) configured to emit light of two wavelength bands (e.g., a red wavelength band and an infrared wavelength band). The PPG sensor may include a light receiving unit (e.g., at least one sensor 260) configured to detect at least a portion of light reflected by or passed through a body part (e.g., a finger, skin of a finger, or a blood vessel) of the user.

According to an embodiment, in order to measure the oxygen saturation of the user, the at least one light emitter 250 may emit light of substantially the same wavelength or each of different wavelengths, and may emit light to a body part (e.g., a finger, a skin of a finger, and/or a blood vessel) of the user. The light emitter 250 may be configured to emit light of a plurality of wavelength bands including a red wavelength and an infrared wavelength. For example, the at least one light emitter 250 may emit light of various bands and may include at least one of a light emitting diode (LED), a laser diode, or a vertical cavity surface emitting laser (VCSEL). At least one light emitter 250 may be disposed and/or mounted on the circuit board 240. The at least one light emitter 250 may be configured to sequentially (or repeatedly) emit light of different wavelength bands by divining time. For example, the light emitter 250 may be configured to emit light through the internal housing portion 213.

According to an embodiment, the at least one sensor 260 may accumulate the optical charge corresponding to the amount of light reflected by or passed through the user's body part and incident thereto, and may convert a biometric signal in the form of an analog current according to the accumulated optical charge into a digital signal. For example, light (or an optical signal) obtained (or detected) through the at least one sensor 260 may be converted through an analog-to-digital converter (ADC) and stored in memory or a sensor buffer. The at least one sensor 260 may include at least one of a photodiode (PD), a photo transistor, a charge-coupled device (CCD), or a complementary metal oxide semiconductor (CMOS). The at least one sensor 260 is not limited thereto, and may include various elements capable of converting an incident optical signal into an electrical signal.

According to an embodiment, the at least one sensor 260 may include a first sensor 261 or a second sensor 263. The first sensor 261 and/or the second sensor 263 may be disposed and/or mounted on the circuit board 240.

According to an embodiment, the first sensor 261 may be disposed farther than the second sensor 263 with respect to the at least one light emitter 250. For example, the first sensor 261 may be positioned farther than the second sensor 263 with respect to the at least one light emitter 250 in the circumferential direction of the housing 210. For example, the distance between the first sensor 261 and the light emitter 250 may be larger than the distance between the second sensor 263 and the light emitter 250.

According to an embodiment, the angle formed by the at least one light emitter 250 and the second sensor 263 with respect to the center O of the wearable electronic device 200 in the ring form may be smaller than the angle formed by the at least one light emitter 250 and the first sensor 261 with respect to the center O of the wearable electronic device 200.

According to an embodiment, the first sensor 261 may be configured to receive light passed through the user's body part. In case the user's body part is not inside the user's body (e.g., a finger), to receive light passed through the user's body part, emitted light propagates through the user's body part. In case the user's body part is inside the user's body (e.g., a blood vessel), to receive light passed through the user's body part, emitted light propagates through the user's body to the user's body part, passes through the user's body part, and the light that passed through the user's body part continues to propagate through the user's body. The first sensor 261 may be referred to as a transmissive sensor. The first sensor 261 may receive at least a portion of the light transferred through the user's body part, convert the transferred light into an electrical signal, and transfer the electrical signal to a processor (e.g., the processor 120 of FIG. 1 or the processor 220 of FIG. 5). According to an embodiment, the second sensor 263 may be configured to receive light reflected by the user's body part. In case the user's body part is not inside the user's body (e.g., a finger), to receive light reflected by the user's body part, emitted light is reflected by the user's body part. In case the user's body part is inside the user's body (e.g., a blood vessel), to receive light reflected by the user's body part, emitted light propagates through the user's body to the user's body part, is reflected by the user's body part, and the light reflected by the user's body part propagates through the user's body. The second sensor 263 may be referred to as a reflective sensor. The second sensor 263 may receive at least a portion of the light reflected by the user's body part, convert the reflected light into an electrical signal, and transfer the electrical signal to a processor (e.g., the processor 120 of FIG. 1 or the processor 220 of FIG. 4).

According to an embodiment, the light emitted from the at least one light emitter 250 may reach the first sensor 261 along a first light path 11 or may reach the second sensor 263 along a second light path 13. For example, the first light path 11 may be a path passed through the user's body part (e.g., a finger, the skin of the finger, or a blood vessel of the finger), and the second light path 13 may be a path reflected by the user's body part. In case the user's body part is not inside the user's body (e.g., a finger), the first light path 11 includes a path through the user's body part, and the second light path 13 includes a path outside the user's body that is reflected by the user's body part. In case the user's body part is inside the user's body (e.g., a blood vessel of a finger), the first light path 11 includes a path inside the user's body that passes through the user's body part inside the user's body, and the second light path 13 includes a path inside the user's body that is reflected by the user's body part inside the user's body.

According to an embodiment, the wearable electronic device 200 may include at least one blocking member 270. At least one blocking member 270 may include a material that absorbs or blocks light. The at least one blocking member 270 may be configured to block light emitted from the at least one light emitter 250 from propagating in the inner space of the housing 210.

According to an embodiment, the at least one blocking member 270 may include a first wall 271 or a second wall 273. The first wall 271 may be positioned between the first sensor 261 and the second sensor 263 in the inner space of the housing 210. The second wall 273 may be positioned between the second sensor 263 and the at least one light emitter 250 in the inner space of the housing 210.

Figure 5:
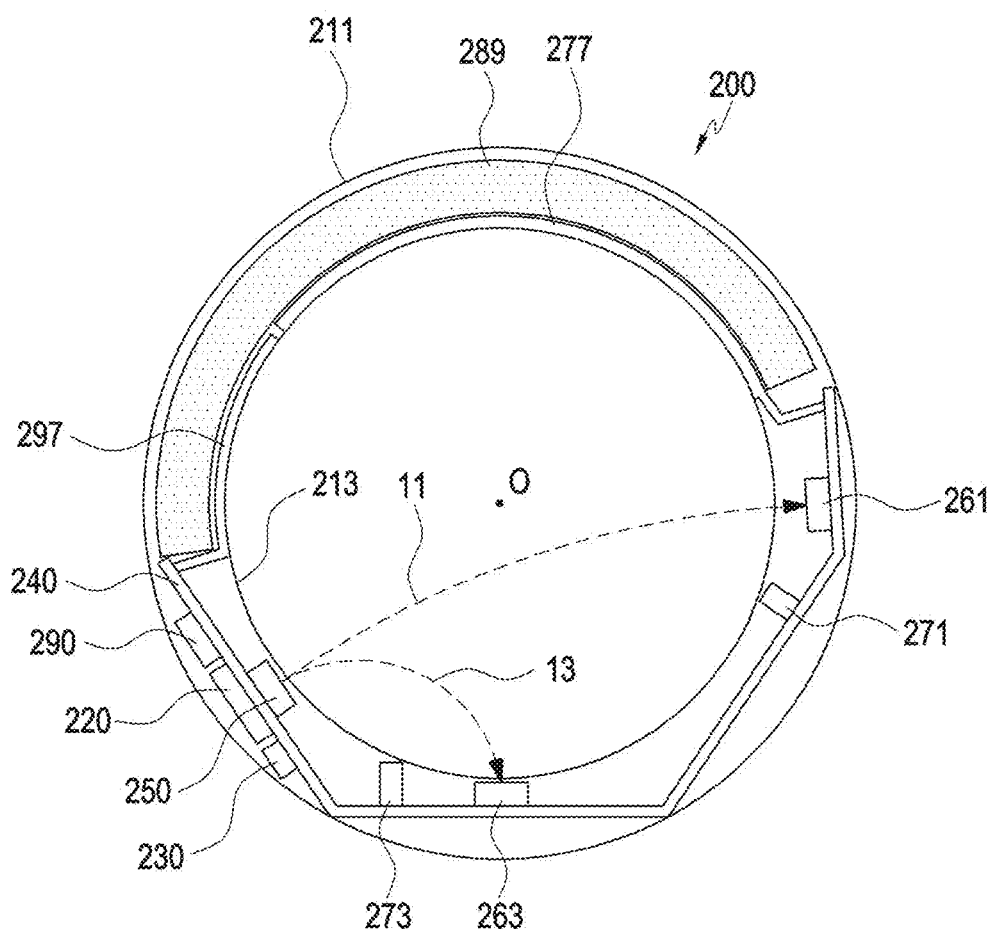
FIG. 5 is a cross-sectional view illustrating a wearable electronic device according to an embodiment of the disclosure.

FIG. 5 is a cross-sectional view illustrating a wearable electronic device according to an embodiment of the disclosure.

Figure 6:
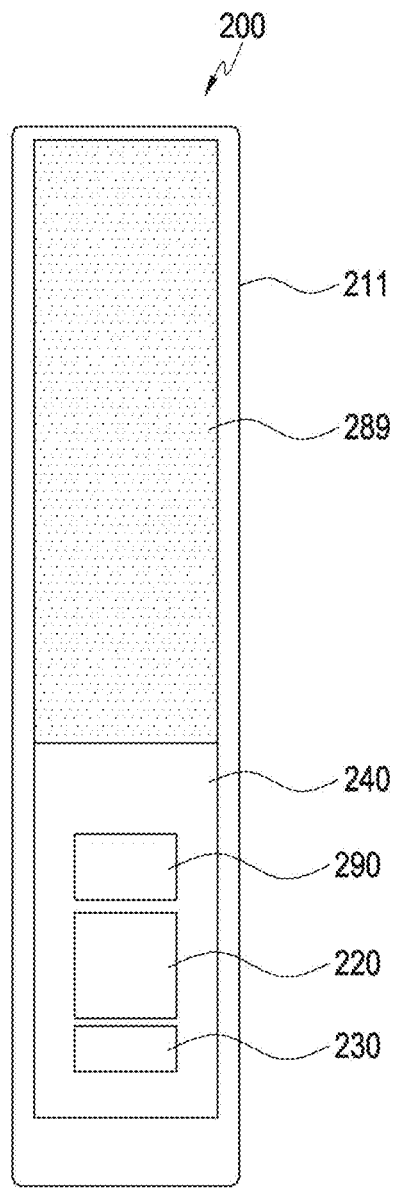
FIG. 6 is a side view illustrating a wearable electronic device according to an embodiment of the disclosure.

FIG. 6 is a side view illustrating a wearable electronic device according to an embodiment of the disclosure.

Figure 7:
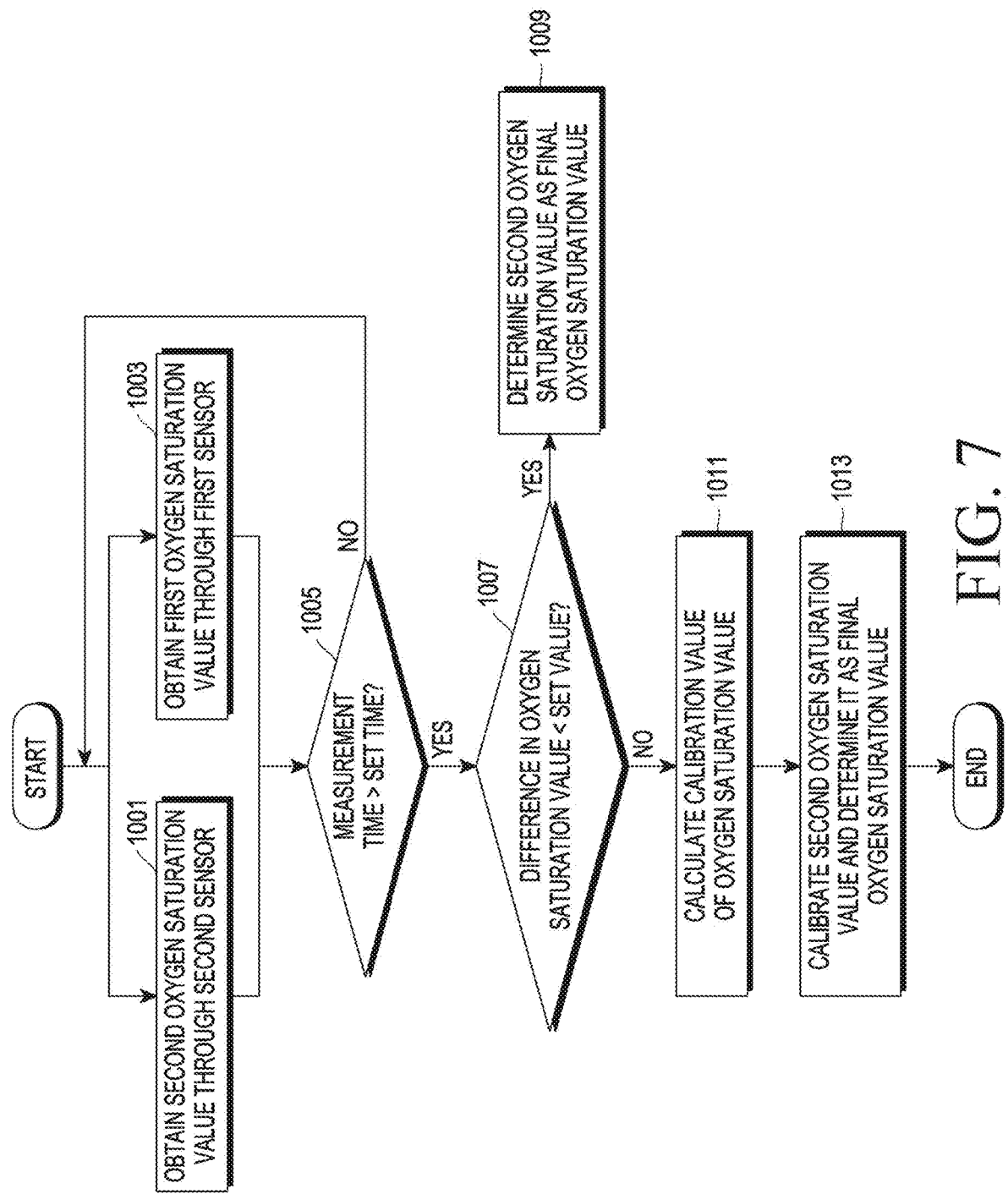
FIG. 7 is a flowchart illustrating a process of obtaining a user's oxygen saturation value according to an embodiment of the disclosure.

FIG. 7 is a flowchart illustrating a process of obtaining a user's oxygen saturation value according to an embodiment of the disclosure.

Figure 8:
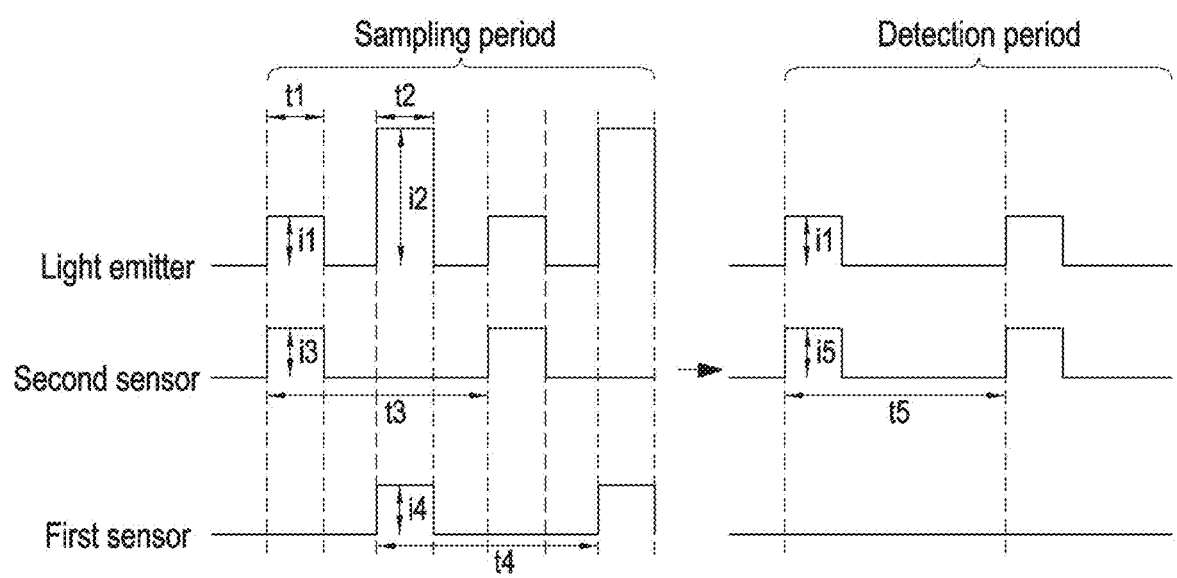
FIG. 8 is a graph illustrating operations of a light emitter and a sensor according to an embodiment of the disclosure.
Figure 9A:
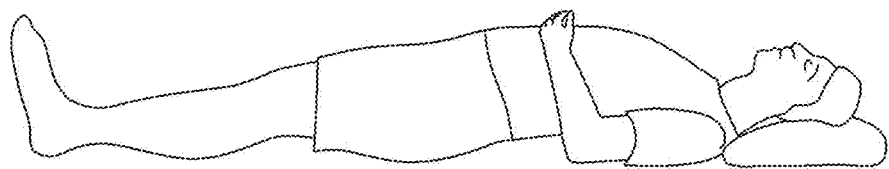
FIGS. 9A, 9B, 9C, and 9D are views illustrating a change in a user's posture according to various embodiments of the disclosure.
Figure 9B:
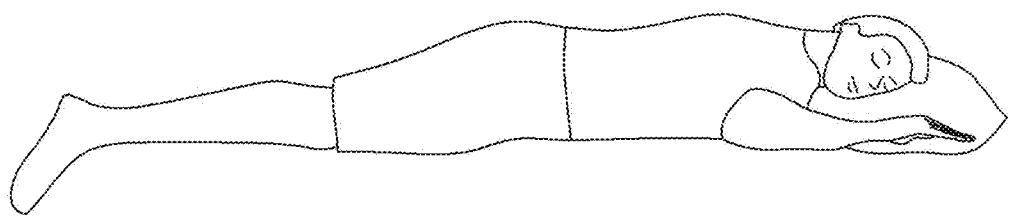
Figure 9C:
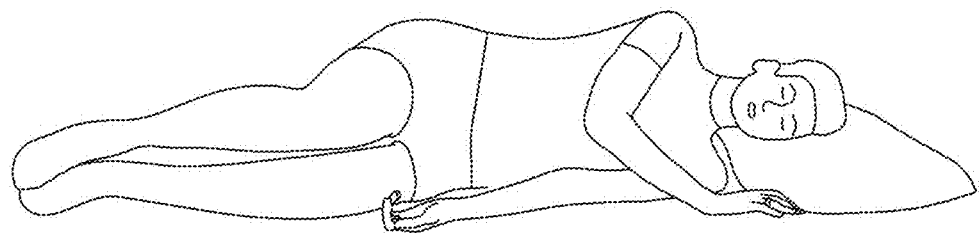
Figure 9D:
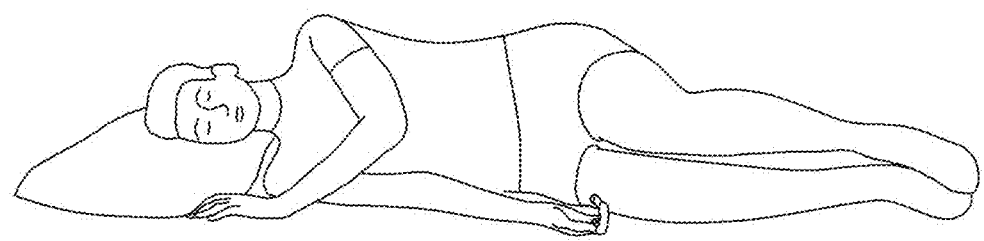

FIG. 8 is a graph illustrating operations of a light emitter and a sensor according to an embodiment of the disclosure.

FIGS. 9A, 9B, 9C, and 9D are views illustrating a change in a user's posture according to various embodiments of the disclosure.

The embodiments of FIGS. 5 to 8 and 9A to 9D may be combined with the embodiments of FIGS. 1 to 4, or the embodiments of FIGS. 10 to 19.

Referring to FIGS. 5 and 6, a wearable electronic device 200 (e.g., the wearable electronic device 200 of FIGS. 2 to 4) may include a housing 210, a processor 220, memory 230, a circuit board 240, at least one light emitter 250, at least one sensor 260, at least one blocking member 270, a charging circuit 277, a battery 289, a communication module 290, or an antenna 297.

The configuration of the housing 210, the circuit board 240, the at least one light emitter 250, the at least one sensor 260, or the at least one blocking member 270 of FIGS. 5 and 6 may be identical in whole or part to the configuration of the housing 210, the circuit board 240, the at least one light emitter 250, the at least one sensor 260, or the at least one blocking member 270 of FIG. 4.

According to an embodiment, the housing 210 may include an external housing portion 211 (e.g., the external housing portion 211 of FIG. 4) and an internal housing portion 213 (e.g., the internal housing portion 213 of FIG. 4) coupled to the external housing portion 211.

According to an embodiment, at least one processor 220 (e.g., the processor 220 of FIG. 1), memory 230 (e.g., the memory 130 of FIG. 1), or a communication module 290 (e.g., the communication module 190 of FIG. 1) may be disposed and/or mounted on the circuit board 240.

According to an embodiment, the at least one processor 220 may include an application processor (AP), a supplementary processor (SP) (e.g., a sensor hub), a central processing unit (CPU), a neural processing unit (NPU), a graphics processing unit (GPU), or an internet of things (IoT) processor (e.g., a processor configured to be integrated with the communication module 290). For example, the processor 220 may control the operation of the wearable electronic device 200. For example, the wearable electronic device 200 and/or the components of the wearable electronic device 200 performing a specific operation may be defined as being controlled by the processor 220. The processor 220 may be defined and/or referred to as a controller.

According to an embodiment, the at least one processor 220 may include processing circuitry. The at least one processor 220 may control the overall operation of the wearable electronic device 200. The at least one processor 220 may include one or more processors. The at least one processor 220 may individually or collectively execute instructions of the memory 230 that cause the wearable electronic device 200 to perform at least one operation.

According to an embodiment, the memory 230 may store data (e.g., sensing data or communication data). The memory 230 may be integrated with the processor 220.

According to an embodiment, the memory 230 may store information for controlling the operation of the wearable electronic device 200. For example, the memory 230 may store instructions. The instructions, when executed individually or collectively by the at least one processor 220, may cause the wearable electronic device 200 or the at least one processor 220 to perform at least one operation. Operations performed by the wearable electronic device 200 and/or the at least one processor 220 described below may be defined and/or interpreted as the instructions being executed to cause the wearable electronic device 200 and/or the at least one processor 220 to perform at least one operation.

According to an embodiment, the communication module 290 may support communication between the wearable electronic device 200 and an external electronic device (e.g., the electronic device 102 or 104 of FIG. 1 or the electronic devices S1 to S8 of FIG. 2).

According to an embodiment, the wearable electronic device 200 may include an antenna 297 (e.g., the antenna module 197 of FIG. 1). The antenna 297 may be an antenna for wireless communication. The antenna 297 may be disposed in an inner space of the housing 210. According to an embodiment, a portion of the housing 210 may be utilized as the antenna 297.

According to an embodiment, the wearable electronic device 200 may include a charging circuit 277. The charging circuit 277 may be configured to support a wired charging (e.g., terminal or pogo pin) method and/or a wireless charging (e.g., wireless power charging (WPC) or NFC) method for charging the battery 289. The wearable electronic device 200 may charge the battery 289 through the charging circuit 277.

According to an embodiment, the wearable electronic device 200 may include a PPG sensor. The PPG sensor may include at least one light emitter 250 (e.g., at least one light emitter 250 of FIG. 4) or at least one sensor 260 (e.g., at least one sensor 260 of FIG. 4).

According to an embodiment, the at least one sensor 260 may include a first sensor 261 (e.g., the first sensor 261 of FIG. 4) or a second sensor 263 (e.g., the second sensor 263 of FIG. 4). The first sensor 261 and/or the second sensor 263 may be configured to receive light emitted from the at least one light emitter 250. The first sensor 261, as a transmissive sensor, may be configured to receive at least a portion of light passed through the user's body part along the first light path 11 (e.g., the first light path 11 of FIG. 4). The second sensor 263, as a reflective sensor, may be configured to receive at least a portion of light reflected by the user's body part along the second light path 13 (e.g., the second light path 13 of FIG. 4).

According to an embodiment, the first sensor 261 may receive at least a portion of light passed through the user's body part (e.g., a finger, the skin of the finger, or a blood vessel of the finger), and the second sensor 263 may receive at least a portion of light reflected by the user's body part.

According to an embodiment, the at least one blocking member 270 may include a first wall 271 (e.g., the first wall 271 of FIG. 4) or a second wall 273 (e.g., the second wall 273 of FIG. 4).

Hereinafter, a process (or an operation method of the wearable electronic device 200) for obtaining an oxygen saturation value (e.g., information on oxygen saturation) of the user is described with reference to FIGS. 7 and 8.

At least some of the operations of FIG. 7 may be performed. The operation order of the operations of FIG. 7 may be changed. At least two of the operations of FIG. 7 may be performed in parallel. Operations other than the operations of FIG. 7 may be performed before, while, or after the operations of FIG. 7 are performed. Operations of FIG. 7 may be defined as being controlled by the wearable electronic device 200 or the processor 220.

According to an embodiment, in operation 1001 and/or operation 1003, the processor 220 may obtain the oxygen saturation value of the user through the at least one sensor 260. The operation of obtaining the oxygen saturation value of the user through the at least one sensor 260 may be an operation (or an operation of generating) of obtaining the oxygen saturation value of the user using a signal (e.g., light) detected by the at least one sensor 260. For example, the processor 220 may obtain the oxygen saturation value of the user based on the electrical signal transferred from the at least one sensor 260. For example, the processor 220 may generate biometric information (e.g., information on oxygen saturation) of the user based on the signal received from the at least one sensor 260.

According to an embodiment, in operation 1001, the processor 220 may obtain the second oxygen saturation value of the user through the second sensor 263. For example, in operation 1001, the processor 220 may control the operation of the at least one light emitter 250 to emit light, and may obtain a second oxygen saturation value of the user using a signal (e.g., light) received from the second sensor 263. For example, in operation 1001, the processor 220 may control the operation of the at least one light emitter 250 to emit light having a first intensity (e.g., the first intensity i1 of FIG. 8). For example, the processor 220 may control the light emitter 250 to emit the second light having the first intensity. Further, the processor 220 may receive a second signal corresponding to the second light through the second sensor 263. In operation 1001, the processor 220 may obtain the second oxygen saturation value of the user by computationally processing the light of the third intensity (e.g., the third intensity i3 of FIG. 8) received from the second sensor 263. For example, since the light received from the second sensor 263 is light reflected by the body part of the user (e.g., light propagating along the second light path 13 of FIG. 5), the intensity may be lower than that emitted from the at least one light emitter 250. In operation 1001, the processor 220 may be configured to allow at least one light emitter 250 to emit light for a first time (e.g., the first time t1 of FIG. 8). The first time t1 may be, e.g., about 36 ms to about 44 ms (millisecond). For example, the first time t1 may be about 40 ms.

According to an embodiment, in operation 1003, the processor 220 may obtain a first oxygen saturation value of the user through the first sensor 261. For example, in operation 1003, the processor 220 may control the operation of the at least one light emitter 250 to emit light, and may obtain a first oxygen saturation value of the user using a signal (e.g., light) received from the first sensor 261. For example, in operation 1003, the processor 220 may control the operation of the at least one light emitter 250 to emit light having a second intensity (e.g., the second intensity i2 of FIG. 8). For example, the processor 220 may control the light emitter 250 to emit the first light having the second intensity. Further, the processor 220 may receive a first signal corresponding to the first light through the first sensor 261. The second intensity i2 may be larger than the first intensity i1. In operation 1003, the processor 220 may obtain the first oxygen saturation value of the user by computationally processing the light of the fourth intensity (e.g., the fourth intensity i4 of FIG. 8) received from the first sensor 261. For example, since the light received from the first sensor 261 is light passed through the user's body part (e.g., light propagating along the first light path 11 of FIG. 5), the intensity may be lower than that emitted from the at least one light emitter 250. In operation 1003, the processor 220 may be configured to allow the at least one light emitter 250 to emit light for a second time (e.g., the second time t2 of FIG. 8). The second time t2 may be, e.g., about 54 ms to about 66 ms (millisecond). For example, the second time t2 may be about 60 ms. The second time t2 may be larger than the first time t1, but is not limited thereto.

According to an embodiment, in operation 1001 and/or operation 1003, the processor 220 may be configured to generate biometric information, based on the received first signal or second signal. The biometric information may include information on oxygen saturation or information on heart rate.

According to an embodiment, the processor 220 may be configured to control the light emitter 250 to emit second light having a first intensity i1 and control the light emitter 250 to emit the first light having a second intensity i2 different from the first intensity i1 after the second light is emitted. The first intensity i1 may be smaller than the second intensity i2.

According to an embodiment, in operation 1001 and/or operation 1003, the light emission intensity of the at least one light emitter 250 may be changed according to the size of the wearable electronic device 200 and/or the distance between the at least one light emitter 250 and the at least one sensor 260.

According to an embodiment, in operation 1005, the processor 220 may be configured to identify whether the measurement time exceeds a set time. For example, the processor 220 may be configured to identify whether the time during which operation 1001 and/or operation 1003 of detecting the oxygen saturation value of the user through the first sensor 261 and/or the second sensor 263 is performed exceeds the set time. For example, the set time may be defined and/or referred to as a sampling period (e.g., the sampling period of FIG. 8). For example, the measurement time may be defined as the time when operation 1001 and/or operation 1003 is performed. If the measurement time is smaller than or equal to the set time, the processor 220 may re-perform operation 1001 and/or operation 1003. For example, the measurement time may be about 15 seconds or more, but is not limited thereto. For example, if the measurement time is smaller than or equal to the set time, the processor 220 may repeat operation 1001 and/or operation 1003 multiple times. In this case, the first oxygen saturation value may be an average value of the oxygen saturation values obtained multiple times, but is not limited thereto. When operation 1001 is performed multiple times, operation 1001 may be repeated every third time (e.g., the third time t3 of FIG. 8). The third time t3 may be larger than the first time t1. Further, the second oxygen saturation value may be an average value of the oxygen saturation values obtained multiple times, but is not limited thereto. When operation 1003 is performed multiple times, operation 1003 may be repeated every fourth time (e.g., the fourth time t4 of FIG. 8). If the measurement time exceeds a set time, the processor 220 may perform operation 1007.

According to an embodiment, in operation 1007, the processor 220 may be configured to identify whether a difference between oxygen saturation values is equal to or smaller than a set value. For example, the difference between the oxygen saturation values may be an error ratio between the first oxygen saturation value and the second oxygen saturation value. For example, the error ratio (%) may be a value obtained by subtracting the first oxygen saturation value from the second oxygen saturation value and then dividing it by the first oxygen saturation value, but is not limited thereto. The set value may be a threshold value set to enhance the reliability (or accuracy) of the oxygen saturation measurement. For example, the set value may be about 4%, but is not limited thereto. In operation 1007, when the difference between the oxygen saturation values is smaller than or equal to the set value, the processor 220 may perform operation 1009. In operation 1007, if the difference between the oxygen saturation values exceeds the set value, the processor 220 may perform operation 1011.

According to an embodiment, in operation 1009, the processor 220 may determine the second oxygen saturation value as the final oxygen saturation value. For example, if the difference between the oxygen saturation values is smaller than or equal to the set value, the difference between the second oxygen saturation value obtained through the second sensor 263 and the first oxygen saturation value obtained through the first sensor 261 may not be large. In operation 1009, the processor 220 may control the at least one light emitter 250 and the second sensor 263 to repeatedly obtain the second oxygen saturation value every fifth time (e.g., the fifth time t5 of FIG. 8). For example, the processor 220 may control the at least one light emitter 250 to emit light of the first intensity i1 in a detection period (e.g., the detection period of FIG. 8), and may obtain the second oxygen saturation value based on the light of the fifth intensity i5 detected by the second sensor 263. The processor 220 may store the repeatedly obtained second oxygen saturation value as the final oxygen saturation value in the memory 230. The processor 220 and/or the communication module 290 may transmit information about the second oxygen saturation value stored in the memory 230 to an external electronic device (e.g., the external electronic device 102 or 104 of FIG. 1 or the electronic devices S1 to S8 of FIG. 2).

According to an embodiment, in operation 1011, the processor 220 may calculate a calibration value of the oxygen saturation value. For example, if the difference between the oxygen saturation values exceeds the set value, the difference between the second oxygen saturation value obtained through the second sensor 263 and the first oxygen saturation value obtained through the first sensor 261 may be large. In operation 1011, the processor 220 may calculate a calibration value obtained by subtracting the second oxygen saturation value from the first oxygen saturation value.

According to an embodiment, in operation 1013, the processor 220 may calibrate the second oxygen saturation value to determine the final oxygen saturation value. For example, if the difference between the oxygen saturation values exceeds the set value, the difference between the second oxygen saturation value obtained through the second sensor 263 and the first oxygen saturation value obtained through the first sensor 261 may be large. In operation 1013, the processor 220 may control the at least one light emitter 250 and the second sensor 263 to repeatedly obtain the second oxygen saturation value every fifth time (e.g., the fifth time t5 of FIG. 8), and may add the calibration value to the obtained second oxygen saturation value. For example, in operation 1013, in the detection period (e.g., the detection period of FIG. 8), the processor 220 may store a value obtained by adding the calibration value to the repeatedly obtained second oxygen saturation value as the final oxygen saturation value in the memory 230. The processor 220 and/or the communication module 290 may transmit information about the final oxygen saturation value stored in the memory 230 to an external electronic device (e.g., the external electronic device 102 or 104 of FIG. 1 or the electronic devices S1 to S8 of FIG. 2).

According to an embodiment, in operation 1009, the processor 220 may be configured to generate biometric information using the second signal, based at least partially on identifying whether the difference between the first signal corresponding to the first light received through the first sensor 261 and the second signal corresponding to the second light received through the second sensor 263 is smaller than or equal to the threshold value.

According to an embodiment, in operations 1011 and 1013, the processor 220 may be configured to generate biometric information by calibrating the second signal based at least partially on identifying that the difference between the first signal corresponding to the first light received through the first sensor 261 and the second signal corresponding to the second light received through the second sensor 263 exceeds the threshold value. In operation 1013, the processor 220 may be configured to generate the biometric information by adding a calibration value corresponding to the difference to the second signal.

According to an embodiment, the processor 220 may be configured to adjust the light emission intensity or the light emission period of the light emitter 250 based at least partially on the difference.

FIGS. 9A, 9B, 9C, and 9D are views illustrating a change in a user's posture. When the user is sleeping, the user's posture may be changed in an unconscious state.

According to an embodiment, the processor 220 may detect a change in the posture of the user. For example, the processor 220 may detect the change in the posture of the user through a sensor (e.g., an acceleration sensor or a gyro sensor) included in the wearable electronic device 200. Further, the processor 220 may interwork with an external electronic device (e.g., the smart watch S8 of FIG. 2) to detect the change in the posture of the user using a sensor (e.g., an acceleration sensor or a gyro sensor) included in the external electronic device.

According to an embodiment, the processor 220 may obtain the oxygen saturation value of the user through the operations 1001, 1003, 1005, 1007, 1009, 1011, and 1013.

According to an embodiment, if the change in the posture of the user is not detected, the processor 220 may obtain the final oxygen saturation value of the user through operation 1009 or may obtain the final oxygen saturation value of the user through operation 1011 and/or operation 1013.

According to an embodiment, if the change in the posture of the user is detected, the processor 220 may re-perform the operations 1001, 1003, 1005, 1007, 1009, 1011, and 1013. For example, if the posture of the user is changed, the relative position or degree of contact between the wearable electronic device 200 and the body part of the user may be changed. In this case, the operations 1001, 1003, 1005, 1007, 1009, 1011, and 1013 may be re-performed to obtain the final oxygen saturation value of the user through operation 1009, or may obtain the final oxygen saturation value of the user through operation 1011 and/or operation 1013.

Figure 10:
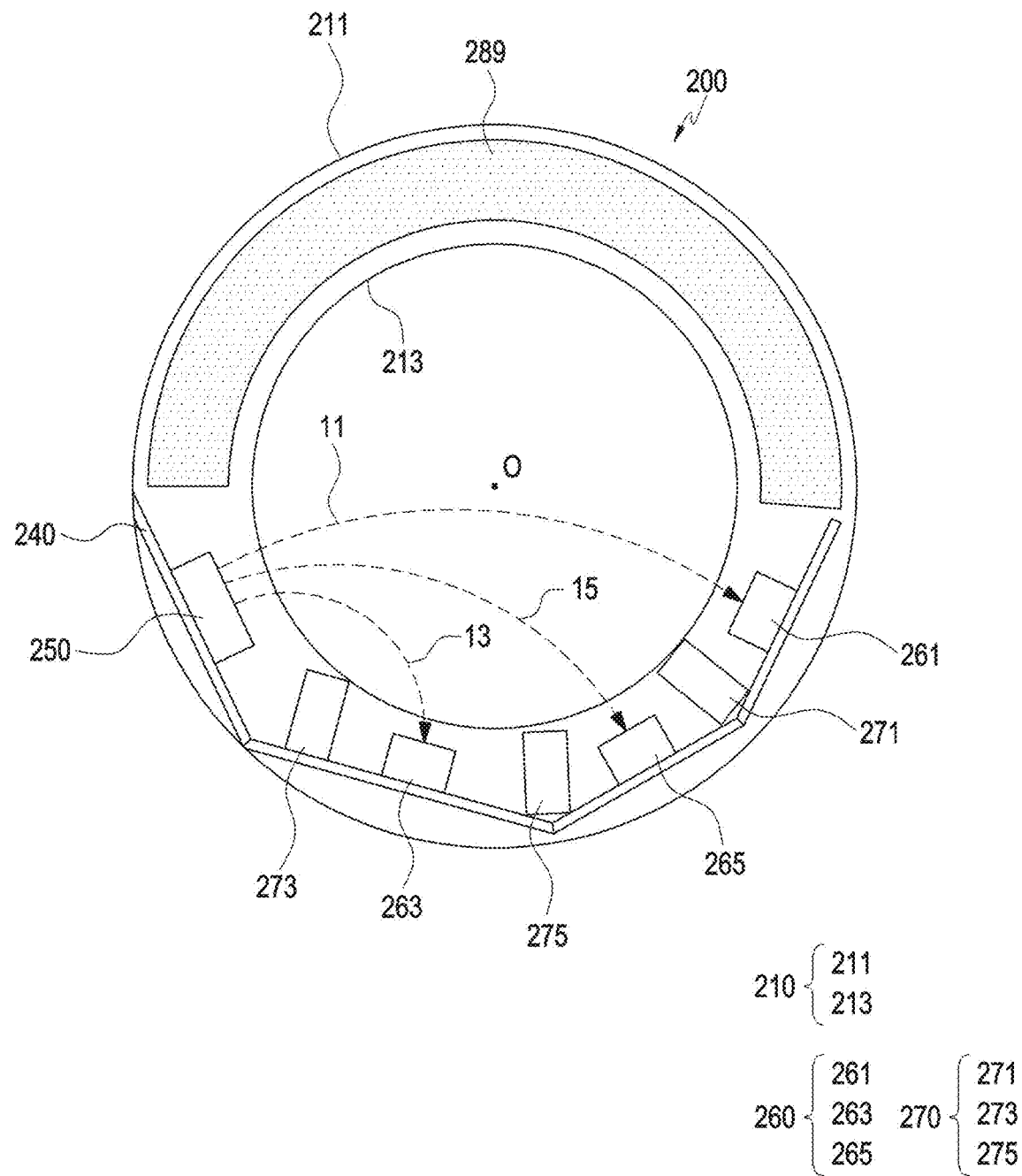
FIG. 10 is a cross-sectional view illustrating a wearable electronic device according to an embodiment of the disclosure.

FIG. 10 is a cross-sectional view illustrating a wearable electronic device according to an embodiment of the disclosure.

Figure 11:
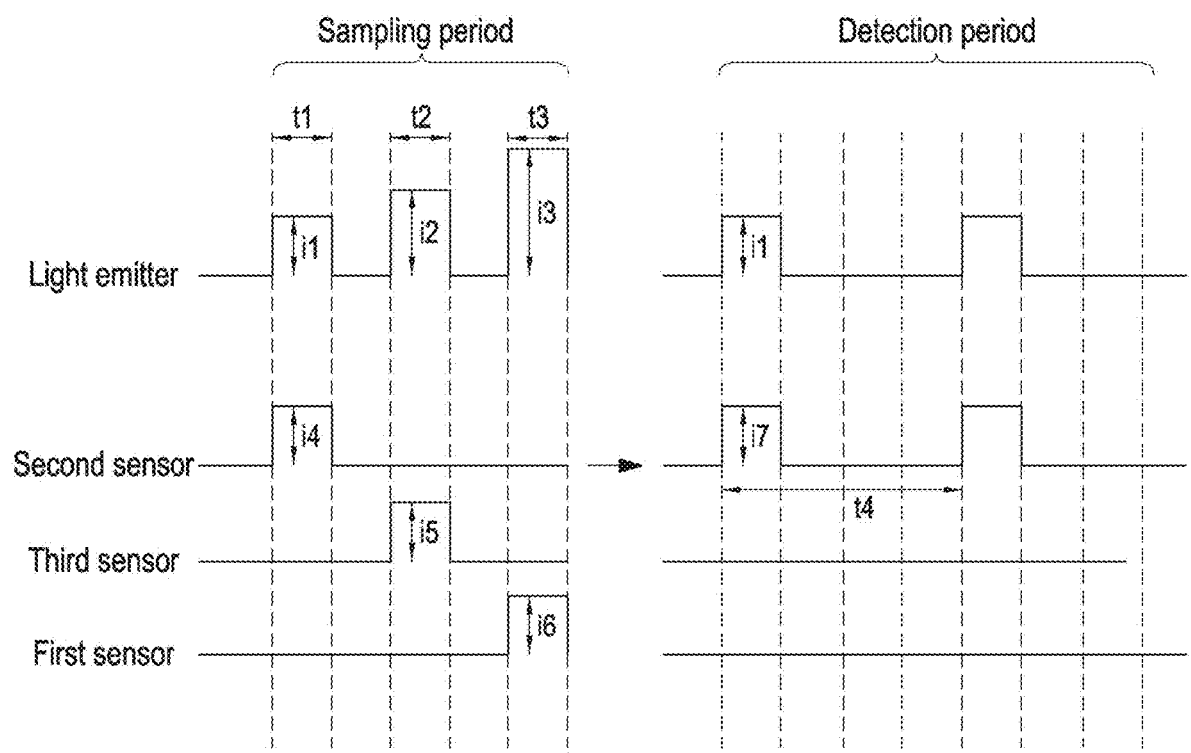
FIG. 11 is a graph illustrating operations of a light emitter and a sensor according to an embodiment of the disclosure.

FIG. 11 is a graph illustrating operations of a light emitter and a sensor according to an embodiment of the disclosure.

The embodiments of FIGS. 10 and 11 may be combined with the embodiments of FIGS. 1 to 8 and 9A to 9D or the embodiments of FIGS. 12 to 19.

Referring to FIGS. 10 and 11, a wearable electronic device 200 (e.g., the wearable electronic device 200 of FIGS. 5 and 6) may include a housing 210, a processor (e.g., the processor 220 of FIG. 5), memory (e.g., the memory 230 of FIG. 5), a circuit board 240, at least one light emitter 250, at least one sensor 260, at least one blocking member 270, a charging circuit (e.g., the charging circuit 277 of FIG. 5), a battery 289, a communication module (e.g., the communication module 290 of FIG. 5), or an antenna (e.g., the antenna 297 of FIG. 5).

The configuration of the housing 210, the processor 220, the memory 230, the circuit board 240, the at least one light emitter 250, the at least one sensor 260, the at least one blocking member 270, or the battery 289 of FIGS. 10 and 11 may be the same in whole or part as the configuration of the housing 210, the circuit board 240, the at least one light emitter 250, the at least one sensor 260, the at least one blocking member 270, or the battery 289 of FIG. 5.

According to an embodiment, the housing 210 may include an external housing portion 211 (e.g., the external housing portion 211 of FIG. 5) and an internal housing portion 213 (e.g., the internal housing portion 213 of FIG. 5) coupled to the external housing portion 211.

According to an embodiment, the at least one sensor 260 may include a first sensor 261 (e.g., the first sensor 261 of FIG. 5), a second sensor 263 (e.g., the second sensor 263 of FIG. 5), or a third sensor 265. The first sensor 261, the second sensor 263, and/or the third sensor 265 may be configured to receive light emitted from the at least one light emitter 250. The first sensor 261 is a transmissive sensor and may be configured to receive light passed through the user's body part along the first light path 11 (e.g., the first light path 11 of FIG. 5). The second sensor 263 is a reflective sensor, and may be configured to receive light reflected by the user's body part along the second light path 13 (e.g., the second light path 13 of FIG. 5). The third sensor 265 is a reflective sensor, and may be configured to receive light reflected by the user's body part along the third light path 15. In case the user's body part is not inside the user's body (e.g., a finger), the third light path 15 includes a path outside the user's body that is reflected by the user's body part. In case the user's body part is inside the user's body (e.g., a blood vessel of a finger), the third light path 15 includes a path inside the user's body that is reflected by the user's body part inside the user's body.

According to an embodiment, the third sensor 265 may be disposed farther than the second sensor 263 with respect to the at least one light emitter 250. For example, the third sensor 265 may be positioned farther than the second sensor 263 with respect to the at least one light emitter 250 in the circumferential direction of the housing 210. According to an embodiment, the angle formed by the at least one light emitter 250 and the third sensor 265 with respect to the center O of the wearable electronic device 200 in the ring form may be larger than the angle formed by the at least one light emitter 250 and the second sensor 263 with respect to the center O of the wearable electronic device 200. The third sensor 265 may be disposed in the housing 210. The third sensor 265 may be positioned between the first sensor 261 and the second sensor 263.

According to an embodiment, the third sensor 265 may be disposed closer to the at least one light emitter 250 than the first sensor 261. For example, the third sensor 265 may be positioned closer to the at least one light emitter 250 than the first sensor 261 in the circumferential direction of the housing 210. For example, with respect to the circumferential direction of the housing 210, the third sensor 265 may be positioned between the first sensor 261 and the second sensor 263. According to an embodiment, the angle formed by the at least one light emitter 250 and the third sensor 265 with respect to the center O of the wearable electronic device 200 in the ring form may be smaller than the angle formed by the at least one light emitter 250 and the first sensor 261 with respect to the center O of the wearable electronic device 200.

According to an embodiment, the third sensor 265 may be disposed and/or mounted on the at least one circuit board 240.

According to an embodiment, the third sensor 265 may be configured to receive light reflected by the user's body part. The third sensor 265 may be referred to as a reflective sensor. The third sensor 265 may receive at least a portion of the light reflected by the user's body part, convert the reflected light into an electrical signal, and transfer the electrical signal to a processor (e.g., the processor 220 of FIG. 5).

According to an embodiment, the light emitted from the at least one light emitter 250 may reach the first sensor 261 along the first light path 11, may reach the second sensor 263 along the second light path 13, or may reach the third sensor 265 through the third light path 15. For example, the first light path 11 may be a path passed through the user's body part (e.g., a finger, the skin of the finger, or a blood vessel of the finger), and the second light path 13 and/or the third light path 15 may be a path reflected by the user's body part.

According to an embodiment, the at least one blocking member 270 may include a first wall 271 (e.g., the first wall 271 of FIG. 5), a second wall 273 (e.g., the second wall 273 of FIG. 5), or a third wall 275.

According to an embodiment, the first wall 271 may be positioned between the first sensor 261 and the third sensor 265 in the inner space of the housing 210. The second wall 273 may be positioned between the second sensor 263 and the at least one light emitter 250 in the inner space of the housing 210. The third wall 275 may be positioned between the third sensor 265 and the second sensor 263 in the inner space of the housing 210.

Hereinafter, a method in which the wearable electronic device 200 (or the processor (e.g., the processor 220 of FIG. 5) detects an oxygen saturation value (e.g., information on the oxygen saturation) of the user is described with reference to FIGS. 11 and 12.

According to an embodiment, in the sampling period, the processor may control the at least one light emitter 250 to obtain a plurality of oxygen saturation values. For example, in the sampling period, the processor may control the at least one light emitter 250 to emit light of different intensities i1, i2, and i3 by dividing time. According to an embodiment, light having different intensities i1, i2, and i3 may be emitted for different times t1, t2, and t3.

According to an embodiment, in the sampling period, the processor may obtain a first oxygen saturation value, based on the light of the sixth intensity i6 detected by the first sensor 261. In the sampling period, the processor may obtain a 2-1th oxygen saturation value based on the light of the fourth intensity i4 detected by the second sensor 263. In the sampling period, the processor may obtain a 2-2th oxygen saturation value based on the light of the fifth intensity i5 detected by the third sensor 265. According to an embodiment, the processor may be configured to receive a first signal corresponding to the first light (e.g., the first light having the third intensity i3) emitted from the light emitter 250 through the first sensor 261. The processor may be configured to receive a second signal corresponding to the second light (e.g., the second light having the first intensity i1) emitted from the light emitter 250 through the second sensor 263. The processor may be configured to receive a third signal corresponding to the third light (e.g., the third light having the second intensity i2) emitted from the light emitter 250 through the third sensor 265.

According to an embodiment, the processor may be configured to generate biometric information (e.g., information on oxygen saturation) using a signal (e.g., a first signal) received through the first sensor 261, a signal (e.g., a second signal) received through the second sensor 263, and a signal (e.g., a third signal) received through the third sensor 265.

According to an embodiment, the processor may be configured to generate biometric information based at least partially on identifying that the difference between the first signal and the third signal is smaller than the difference between the second signal and the second signal.

According to an embodiment, the processor may be configured to generate biometric information based at least partially on identifying that the difference between the first signal and the third signal exceeds the difference between the second signal and the second signal.

According to an embodiment, in the sampling period, the processor may determine a value having the smallest difference from the first oxygen saturation value, of the 2-1th oxygen saturation value and the 2-2th oxygen saturation value. For example, if the 2-1th oxygen saturation value compared with the 2-2th oxygen saturation value corresponds to a value close to the first oxygen saturation value, the processor may determine the 2-1th oxygen saturation value as the second oxygen saturation value. In this case, the processor may obtain a final oxygen saturation value using the second sensor 263 and the first sensor 261. For example, if the difference between the second oxygen saturation value and the first oxygen saturation value obtained in the sampling period is smaller than or equal to the set value, the processor may determine the second oxygen saturation value obtained using the light of the seventh intensity i7 detected through the second sensor 263 in the detection period as the final oxygen saturation value. For example, if the difference between the second oxygen saturation value and the first oxygen saturation value obtained in the sampling period exceeds the set value, the processor may determine the value obtained by calibrating the second oxygen saturation value obtained using the light of the seventh intensity i7 detected through the second sensor 263 in the detection period based on the calibration value (e.g., the calibrate value using the first oxygen saturation value and the second oxygen saturation value) as the final oxygen saturation value. In the detection period, the processor may control the at least one light emitter 250 and the second sensor 263 to repeatedly obtain the second oxygen saturation value (or a final oxygen saturation value) every fourth time t4.

Figure 12:
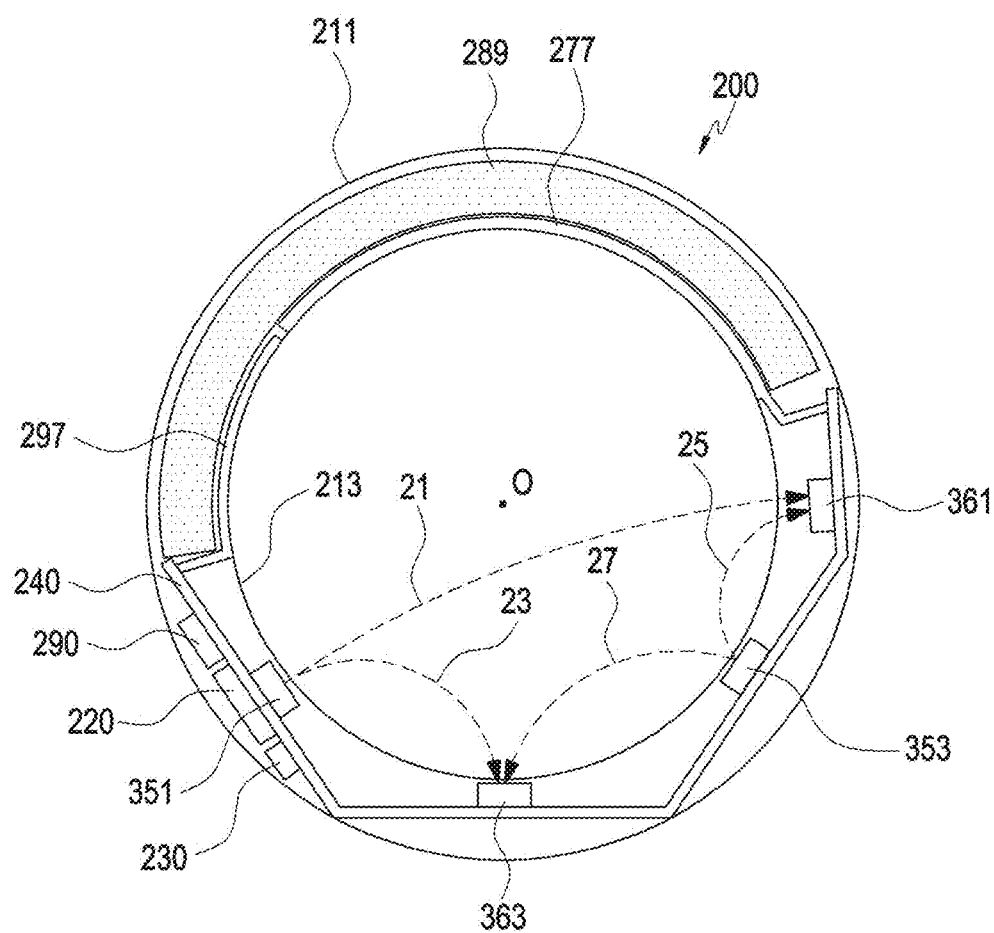
FIG. 12 is a cross-sectional view illustrating a wearable electronic device according to an embodiment of the disclosure.

FIG. 12 is a cross-sectional view illustrating a wearable electronic device according to an embodiment of the disclosure.

Figure 13:
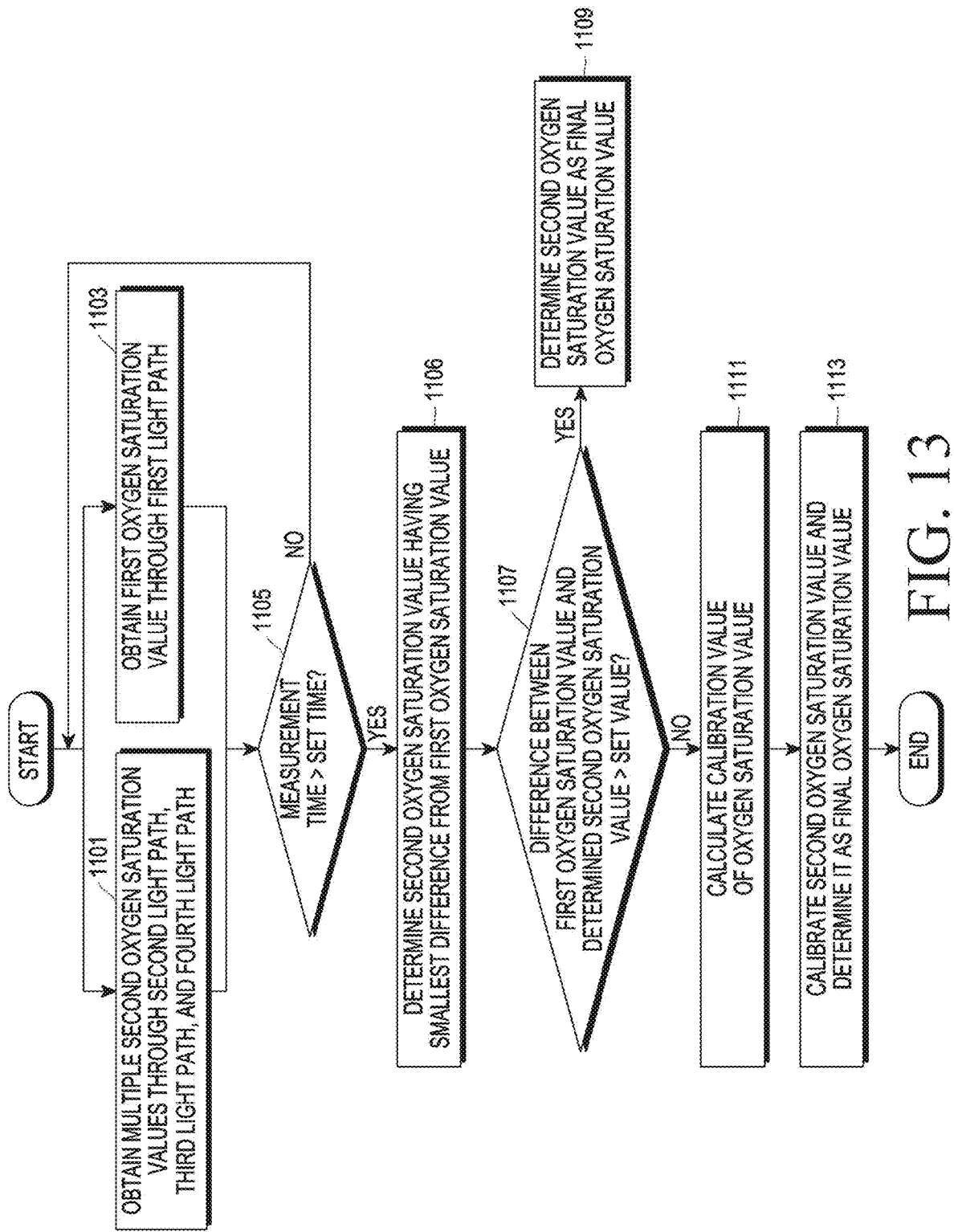
FIG. 13 is a flowchart illustrating a process of obtaining a user's oxygen saturation value according to an embodiment of the disclosure.

FIG. 13 is a flowchart illustrating a process of obtaining a user's oxygen saturation value according to an embodiment of the disclosure.

Figure 14:
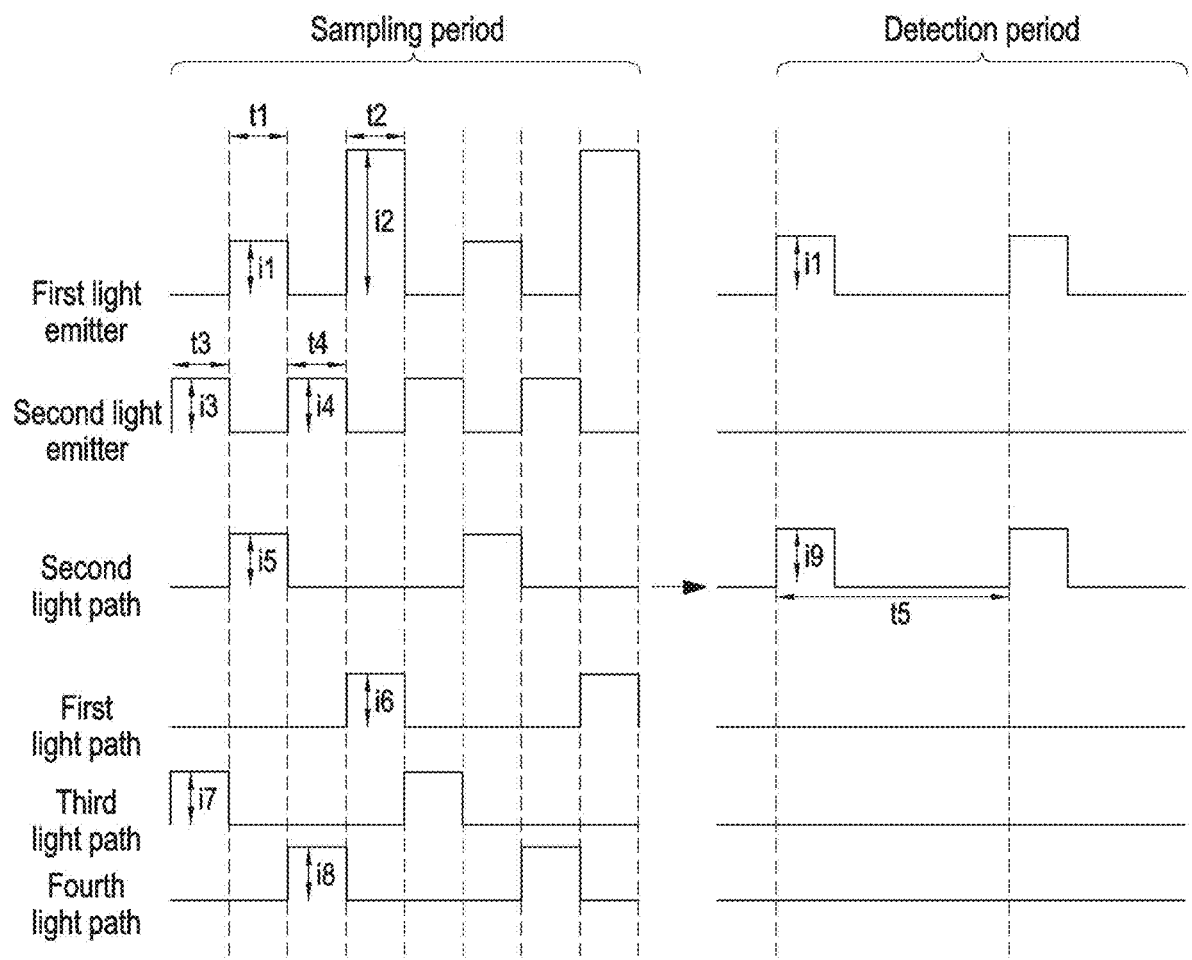
FIG. 14 is a graph illustrating operations of a light emitter and a sensor according to an embodiment of the disclosure.

FIG. 14 is a graph illustrating operations of a light emitter and a sensor according to an embodiment of the disclosure.

The embodiments of FIGS. 12 and 14 may be combined with the embodiments of FIGS. 1 to 8, 9A to 9D, and 10 or the embodiments of FIGS. 15 to 19.

Referring to FIGS. 12 to 14, a wearable electronic device 200 (e.g., the wearable electronic device 200 of FIGS. 2 to 6, or the wearable electronic device 200 of FIG. 10) may include a housing 210, a processor 220, memory 230, a circuit board 240, at least one light emitter 250, at least one sensor 260, a charging circuit 277, a battery 289, a communication module 290, or an antenna 297.

The configuration of the housing 210, the processor 220, the memory 230, the circuit board 240, the at least one light emitter 250, the at least one sensor 260, the charging circuit 277, the battery 289, the communication module 290, or the antenna 297 of FIGS. 12 to 14 may be the same in whole or part as the configuration of the housing 210, the processor 220, the memory 230, the circuit board 240, the at least one light emitter 250, the at least one sensor 260, the charging circuit 277, the battery 289, the communication module 290, or the antenna 297 of FIG. 5.

According to an embodiment, the housing 210 may include an external housing portion 211 (e.g., the external housing portion 211 of FIG. 5) and an internal housing portion 213 (e.g., the internal housing portion 213 of FIG. 5) coupled to the external housing portion 211.

According to an embodiment, the processor 220, the memory 230, or the communication module 290 may be disposed and/or mounted on the circuit board 240.

According to an embodiment, the at least one light emitter 250 may include a first light emitter 351 or a second light emitter 353. The first light emitter 351 and/or the second light emitter 353 may be disposed and/or mounted on the circuit board 240. According to an embodiment, the first light emitter 351 and/or the second light emitter 353 each may emit light of substantially the same wavelength or different wavelengths to measure the user's oxygen saturation to emit light to the user's body part (e.g., a finger, the skin of the finger, and/or a blood vessel).

According to an embodiment, the second light emitter 353 may be positioned between the first sensor 361 and the second sensor 363 along the circumferential direction of the housing 210 with respect to the center O of the wearable electronic device 200.

According to an embodiment, the at least one sensor 260 may include a first sensor 361 (e.g., the first sensor 261 of FIG. 5) or a second sensor 363 (e.g., the second sensor 263 of FIG. 5). The first sensor 361 and/or the second sensor 363 may be configured to receive light emitted from the at least one light emitter 250. The first sensor 361 may be configured to receive at least a portion of light passed through the user's body part along the first light path 21 (e.g., the first light path 11 of FIG. 5) or receive at least a portion of light reflected by the user's body part along the third light path 25. The second sensor 363 may be configured to receive at least a portion of the light reflected by the user's body part along the second light path 23 (e.g., the second light path 13 of FIG. 5) or at least a portion of the light reflected by the user's body part along the fourth light path 27. In case the user's body part is not inside the user's body (e.g., a finger), the first light path 21 includes a path through the user's body part, the second light path 23 includes a path outside the user's body that is reflected by the user's body part, the third light path 25 includes a path outside the user's body that is reflected by the user's body part, and the fourth light path 27 includes a path outside the user's body that is reflected by the user's body part. In case the user's body part is inside the user's body (e.g., a blood vessel of a finger), the first light path 21 includes a path inside the user's body that passes through the user's body part inside the user's body, the second light path 23 includes a path inside the user's body that is reflected by the user's body part inside the user's body, the third light path 25 includes a path inside the user's body that is reflected by the user's body part inside the user's body, and the fourth light path 27 includes a path inside the user's body that is reflected by the user's body part inside the user's body.

According to an embodiment, the light emitted from the first light emitter 351 may be passed through the user's body part and received by the first sensor 361 (see the first light path 21), or may be reflected by the user's body part and received by the second sensor 363 (see the second light path 23). The light emitted from the second light emitter 353 may be reflected by the body part of the user and received by the first sensor 361 (see the third light path 25), or reflected by the body part of the user and received by the second sensor 363 (see the fourth light path 27).

Hereinafter, a process (or an operation method of the wearable electronic device 200) for obtaining an oxygen saturation value (e.g., information on oxygen saturation) of the user is described with reference to FIGS. 13 and 14.

At least some of the operations of FIG. 13 may be performed. The operation order of the operations of FIG. 13 may be changed. At least two of the operations of FIG. 13 may be performed in parallel. Operations other than the operations of FIG. 13 may be performed before, while, or after the operations of FIG. 13 are performed. Operations of FIG. 13 may be defined as being controlled by the wearable electronic device 200 or the processor 220.

According to an embodiment, in operation 1101 and/or operation 1103, the processor 220 may obtain the oxygen saturation value of the user through the at least one sensor 260. The operation of obtaining the oxygen saturation value of the user through the at least one sensor 260 may be an operation (or an operation of generating) of obtaining the oxygen saturation value of the user using a signal (e.g., light) detected by the at least one sensor 260. For example, the processor 220 may obtain the oxygen saturation value of the user based on the electrical signal transferred from the at least one sensor 260. For example, the processor 220 may generate biometric information (e.g., information on oxygen saturation) of the user based on the signal received from the at least one sensor 260.

According to an embodiment, in operation 1101, the processor 220 may obtain the second oxygen saturation value of the user through the second light path 23, the third light path 25, and the fourth light path 27.

According to an embodiment, in operation 1101, the processor 220 may control the operation of the first light emitter 351 to emit light, and may obtain the 2-1th oxygen saturation value of the user using the signal (e.g., light) received from the second sensor 363 through the second light path (e.g., the second light path 23 of FIG. 12). For example, in operation 1101, the processor 220 may control the operation of the first light emitter 351 to emit light having the first intensity (e.g., the first intensity i1 of FIG. 14). In operation 1101, the processor 220 may obtain the 2-1th oxygen saturation value of the user by computationally processing the light of the fifth intensity (e.g., the fifth intensity i5 of FIG. 14) received from the second sensor 363.

For example, the processor 220 may receive a signal corresponding to light having the first intensity i1 through the second sensor 363. For example, since the light received from the second sensor 363 is light reflected by the body part of the user (e.g., light propagating along the second light path 23 of FIG. 12), the intensity may be lower than that of the light emitted from the first light emitter 351. In operation 1101, the processor 220 may be configured to allow a first light emitter 351 to emit light for a first time (e.g., the first time t1 of FIG. 14).

According to an embodiment, in operation 1101, the processor 220 may control the operation of the second light emitter 353 to emit light, and may obtain the 2-2th oxygen saturation value of the user using the signal (e.g., light) received from the first sensor 361 through the third light path (e.g., the third light path 25 of FIG. 12). For example, in operation 1101, the processor 220 may control the operation of the second light emitter 353 to emit light having the third intensity (e.g., the third intensity i3 of FIG. 14). In operation 1101, the processor 220 may obtain the 2-2th oxygen saturation value of the user by computationally processing the light of the third intensity (e.g., the seventh intensity i7 of FIG. 14) received from the first sensor 361. For example, the processor 220 may receive a signal corresponding to light having the third intensity i3 through the first sensor 361. For example, since the light received from the first sensor 361 is light reflected by the body part of the user (e.g., light propagating along the third light path 25 of FIG. 12), the intensity may be lower than that of the light emitted from the second light emitter 353. In operation 1101, the processor 220 may be configured to allow the second light emitter 353 to emit light for a first time (e.g., the third time t3 of FIG. 14).

According to an embodiment, in operation 1101, the processor 220 may control the operation of the second light emitter 353 to emit light, and may obtain the 2-3th oxygen saturation value of the user using the signal (e.g., light) received from the second sensor 363 through the fourth light path (e.g., the fourth light path 27 of FIG. 12). For example, in operation 1101, the processor 220 may control the operation of the second light emitter 353 to emit light having the fourth intensity (e.g., the fourth intensity i4 of FIG. 14). In operation 1101, the processor 220 may obtain the 2-3th oxygen saturation value of the user by computationally processing the light of the eighth intensity (e.g., the eighth intensity i8 of FIG. 14) received from the second sensor 363. For example, the processor 220 may receive a signal corresponding to light having the fourth intensity i4 through the second sensor 363. For example, since the light received from the second sensor 363 is light reflected by the body part of the user (e.g., light propagating along the fourth light path 27 of FIG. 12), the intensity may be lower than that of the light emitted from the second light emitter 353. In operation 1101, the processor 220 may be configured to allow the second light emitter 353 to emit light for a first time (e.g., the fourth time t4 of FIG. 14).

According to an embodiment, in operation 1103, the processor 220 may obtain a first oxygen saturation value of the user through the first sensor 361. For example, in operation 1103, the processor 220 may control the operation of the first light emitter 351 to emit light, and may obtain a first oxygen saturation value of the user using a signal (e.g., light) received from the first sensor 361. For example, in operation 1103, the processor 220 may control the operation of the first light emitter 351 to emit light having the second intensity (e.g., the second intensity i2 of FIG. 14). The second intensity i2 may be larger than the first intensity i1, the third intensity i3, or the fourth intensity i4. In operation 1103, the processor 220 may obtain the first oxygen saturation value of the user by computationally processing the light of the sixth intensity (e.g., the sixth intensity i6 of FIG. 14) received from the first sensor 361. For example, the processor 220 may receive a signal corresponding to light having the second intensity i2 through the first sensor 361. For example, since the light received from the first sensor 361 is light reflected by the body part of the user (e.g., light propagating along the first light path 21 of FIG. 12), the intensity may be lower than that of the light emitted from the first light emitter 351. In operation 1103, the processor 220 may be configured to allow the first light emitter 351 to emit light for a second time (e.g., the second time t2 of FIG. 14). The second time t2 may be larger than the first time t1, the third time t3, or the fourth time t4.

According to an embodiment, in operation 1101 and/or operation 1103, the light emission intensity of the first light emitter 351 and/or the second light emitter 353 may be changed according to the size of the wearable electronic device 200 and/or the distance between the at least one light emitter 350 and the at least one sensor 360.

According to an embodiment, in operation 1105, the processor 220 may be configured to identify whether the measurement time exceeds a set time. For example, the processor 220 may be configured to identify whether the time during which operation 1101 and/or operation 1103 of detecting the oxygen saturation value of the user through the first sensor 361 and/or the second sensor 363 is performed exceeds the set time. For example, the set time may be defined and/or referred to as a sampling period (e.g., the sampling period of FIG. 14). For example, the measurement time may be defined as the time when operation 1101 and/or operation 1103 is performed. If the measurement time is smaller than or equal to the set time, the processor 220 may re-perform operation 1101 and/or operation 1103. For example, the measurement time may be about 15 seconds or more, but is not limited thereto. For example, if the measurement time is smaller than or equal to the set time, the processor 220 may repeat operation 1101 and/or operation 1103 multiple times. In this case, the first oxygen saturation value may be an average value of the oxygen saturation values obtained multiple times, but is not limited thereto. Each of the 2-1th oxygen saturation value, the 2-2th oxygen saturation value, and the 2-3th oxygen saturation value may be an average value of oxygen saturation values obtained multiple times, but is not limited thereto. If the measurement time exceeds a set time, the processor 220 may perform operation 1106.

According to an embodiment, in operation 1106, the processor 220 may determine the second oxygen saturation value having the smallest difference from the first oxygen saturation value. For example, the processor 220 may determine a value closest to the first oxygen saturation value obtained in the sampling period from among the 2-1th oxygen saturation value, the 2-2th oxygen saturation value, and the 2-3th oxygen saturation value obtained in the sampling period. For example, if the 2-1th oxygen saturation value is the same as or closest to the first oxygen saturation value, the processor 220 may determine the 2-1th oxygen saturation value as the second oxygen saturation value. Hereinafter, operation 1107, operation 1109, operation 1111, and/or operation 1113 is described with an example in which the 2-1th oxygen saturation value is determined as the second oxygen saturation value, but the description thereof may be equally applied and/or understood even when the 2-2th oxygen saturation value and/or the 2-3th oxygen saturation value are determined as the second oxygen saturation value.

According to an embodiment, in operation 1107, the processor 220 may be configured to identify whether a difference between oxygen saturation values is equal to or smaller than a set value. For example, the difference between the oxygen saturation values may be an error ratio between the first oxygen saturation value and the determined second oxygen saturation value (e.g., the second oxygen saturation value determined in operation 1106). For example, the error ratio (%) may be a value obtained by subtracting the first oxygen saturation value from the determined second oxygen saturation value and then dividing it by the first oxygen saturation value, but is not limited thereto. The set value may be a threshold value set to enhance the reliability (or accuracy) of the oxygen saturation measurement. For example, the set value may be about 4%, but is not limited thereto. In operation 1107, when the difference between the oxygen saturation values is smaller than or equal to the set value, the processor 220 may perform operation 1109. In operation 1107, if the difference between the oxygen saturation values exceeds the set value, the processor 220 may perform operation 1111.

According to an embodiment, in operation 1109, the processor 220 may determine the determined second oxygen saturation value as the final oxygen saturation value. For example, if the difference between the oxygen saturation values is smaller than or equal to the set value, the difference between the second oxygen saturation value obtained through the second sensor 363 and the first oxygen saturation value obtained through the first sensor 361 may not be large. In operation 1109, the processor 220 may control the first light emitter 351 and the second sensor 363 to repeatedly obtain the second oxygen saturation value every fifth time (e.g., the fifth time t5 of FIG. 14). For example, the processor 220 may control the at least one light emitter 250 to emit light of the first intensity i1 in a detection period (e.g., the detection period of FIG. 14), and may obtain the second oxygen saturation value based on the light of the ninth intensity 19 detected by the second sensor 363. The processor 220 may store the repeatedly obtained second oxygen saturation value as the final oxygen saturation value in the memory 230. The processor 220 and/or the communication module 290 may transmit information about the second oxygen saturation value stored in the memory 230 to an external electronic device (e.g., the external electronic device 102 or 104 of FIG. 1 or the electronic devices S1 to S8 of FIG. 2).

According to an embodiment, in operation 1111, the processor 220 may calculate a calibration value of the oxygen saturation value. For example, if the difference between the oxygen saturation values exceeds the set value, the difference between the second oxygen saturation value obtained through the second sensor 363 and the first oxygen saturation value obtained through the first sensor 361 may be large. In operation 1111, the processor 220 may calculate a calibration value obtained by subtracting the second oxygen saturation value from the first oxygen saturation value.

According to an embodiment, in operation 1113, the processor 220 may calibrate the second oxygen saturation value to determine the final oxygen saturation value. For example, if the difference between the oxygen saturation values exceeds the set value, the difference between the second oxygen saturation value obtained through the second sensor 363 and the first oxygen saturation value obtained through the first sensor 361 may be large. In operation 1113, the processor 220 may control the first light emitter 351 and the second sensor 363 to repeatedly obtain the second oxygen saturation value every fifth time (e.g., the fifth time t5 of FIG. 14), and may add the calibration value to the obtained second oxygen saturation value. For example, in operation 1113, in the detection period (e.g., the detection period of FIG. 14), the processor 220 may store a value obtained by adding the calibration value to the repeatedly obtained second oxygen saturation value as the final oxygen saturation value in the memory 230. The processor 220 and/or the communication module 290 may transmit information about the final oxygen saturation value stored in the memory 230 to an external electronic device (e.g., the external electronic device 102 or 104 of FIG. 1 or the electronic devices S1 to S8 of FIG. 2).

According to an embodiment, the processor 220 may detect a change in the posture of the user. For example, the processor 220 may detect the change in the posture of the user through a sensor (e.g., an acceleration sensor or a gyro sensor) included in the wearable electronic device 200. Further, the processor 220 may interwork with an external electronic device (e.g., the smart watch S8 of FIG. 2) to detect the change in the posture of the user using a sensor (e.g., an acceleration sensor or a gyro sensor) included in the external electronic device.

According to an embodiment, the processor 220 may obtain the oxygen saturation value of the user through the operations 1101, 1103, 1105, 1106, 1107, 1109, 1111, and 1113.

According to an embodiment, if the change in the posture of the user is not detected, the processor 220 may obtain the final oxygen saturation value of the user through operation 1109 or may obtain the final oxygen saturation value of the user through operation 1111 and/or operation 1113.

According to an embodiment, if the change in the posture of the user is detected, the processor 220 may re-perform the operations 1101, 1103, 1105, 1106, 1107, 1109, 1111, and 1113. For example, if the posture of the user is changed, the relative position or degree of contact between the wearable electronic device 200 and the body part of the user may be changed. In this case, the operations 1101, 1103, 1105, 1106, 1107, 1109, 1111, and 1113 may be re-performed to obtain the final oxygen saturation value of the user through operation 1109, or may obtain the final oxygen saturation value of the user through operation 1111 and/or operation 1113.

Figure 15:
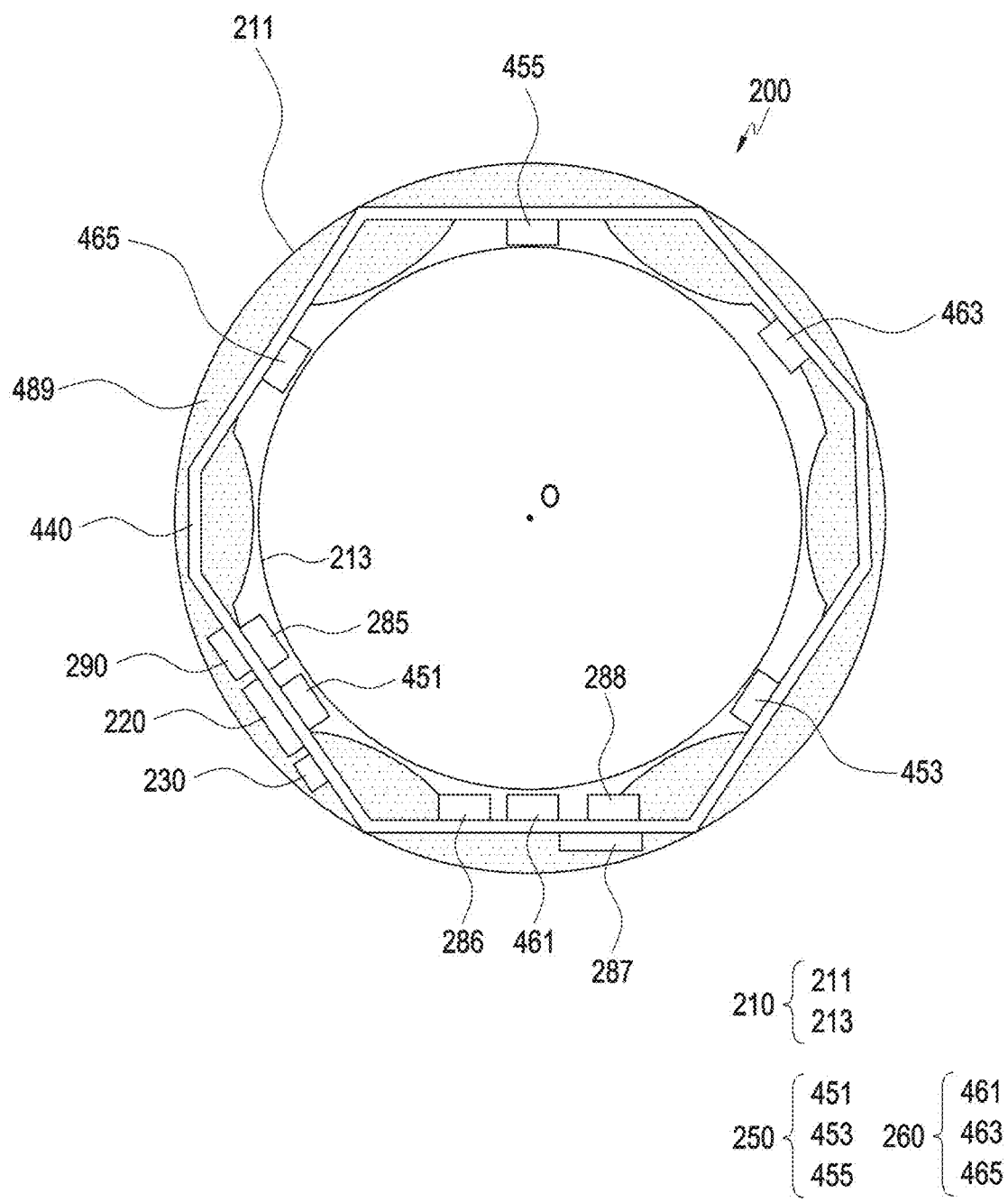
FIG. 15 is a cross-sectional view illustrating a wearable electronic device according to an embodiment of the disclosure.

FIG. 15 is a cross-sectional view illustrating a wearable electronic device according to an embodiment of the disclosure.

Figure 16:
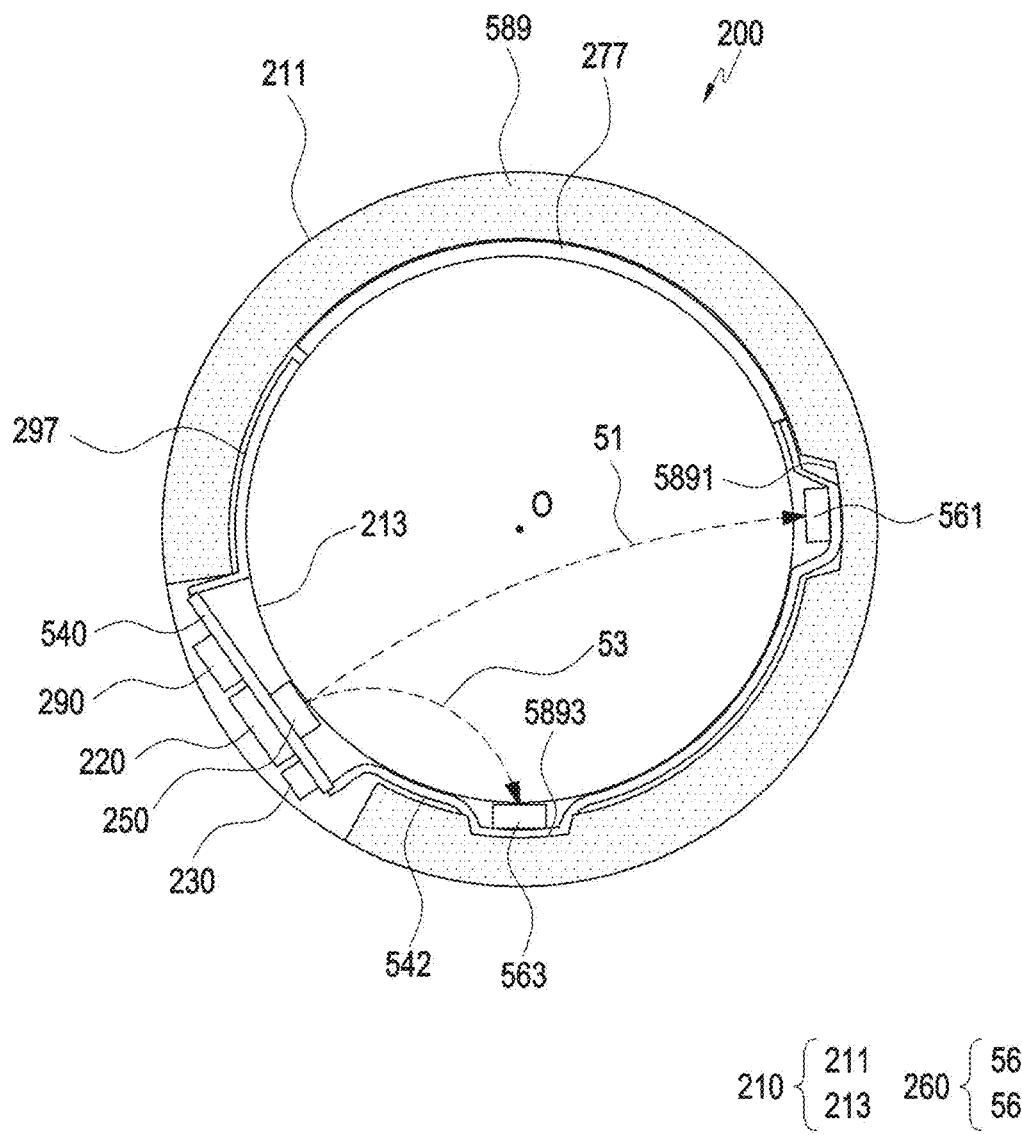
FIG. 16 is a cross-sectional view illustrating a wearable electronic device according to an embodiment of the disclosure.

FIG. 16 is a cross-sectional view illustrating a wearable electronic device according to an embodiment of the disclosure.

Figure 17:
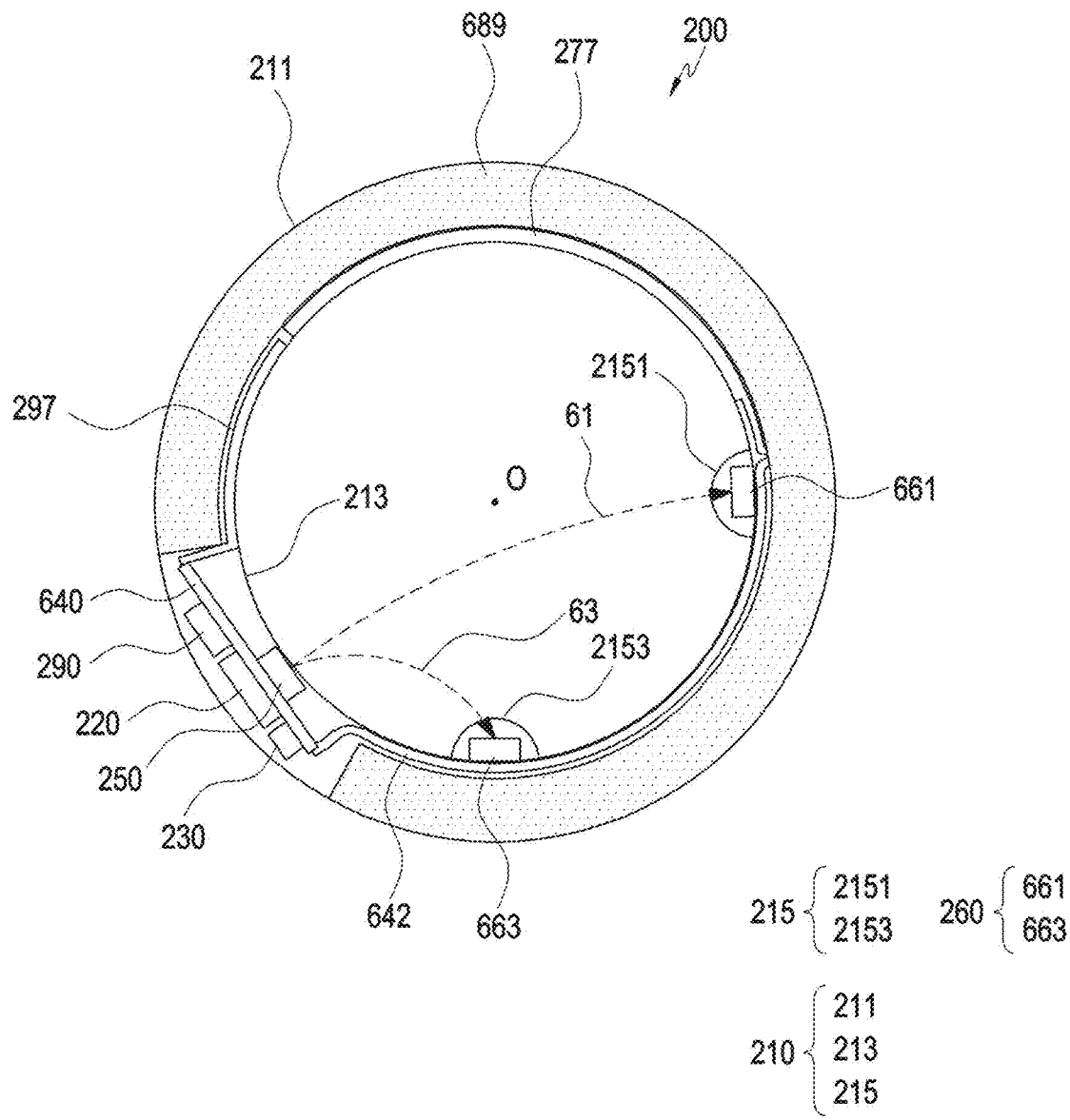
FIG. 17 is a cross-sectional view illustrating a wearable electronic device according to an embodiment of the disclosure.

FIG. 17 is a cross-sectional view illustrating a wearable electronic device according to an embodiment of the disclosure.

Figure 18:
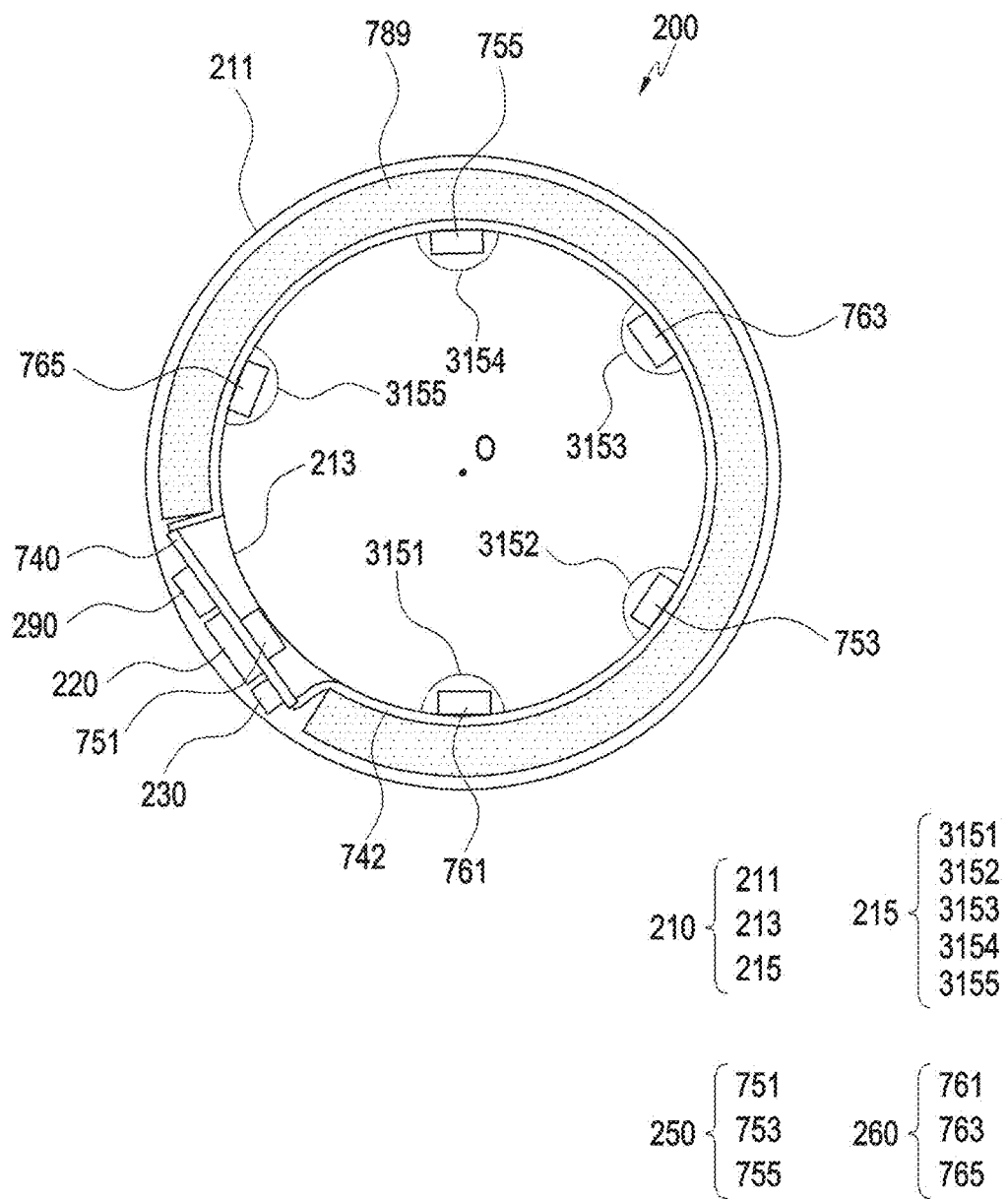
FIG. 18 is a cross-sectional view illustrating a wearable electronic device according to an embodiment of the disclosure.

FIG. 18 is a cross-sectional view illustrating a wearable electronic device according to an embodiment of the disclosure.

Figure 19:
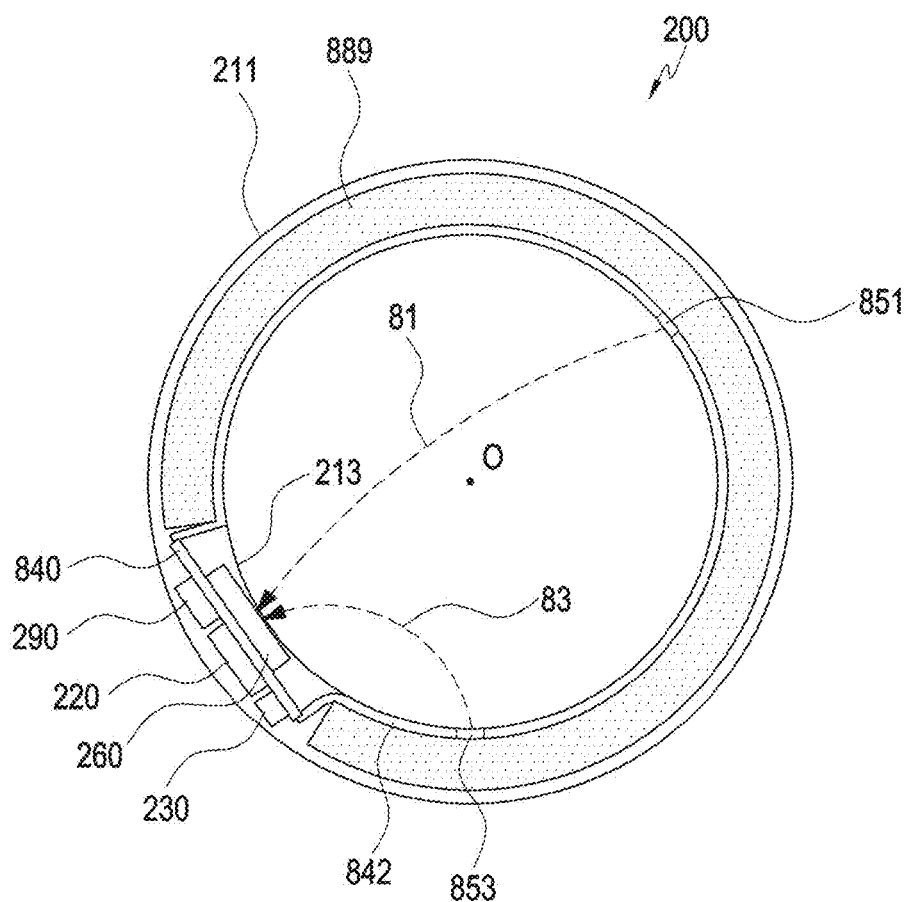
FIG. 19 is a cross-sectional view illustrating a wearable electronic device according to an embodiment of the disclosure.

FIG. 19 is a cross-sectional view illustrating a wearable electronic device according to an embodiment of the disclosure.

The embodiments of FIGS. 15 to 19 may be combined with the embodiments of FIGS. 1 to 8, 9A to 9D, and 10 to 14.

Referring to FIGS. 15 to 19, a wearable electronic device 200 (e.g., the wearable electronic device 200 of FIGS. 2 to 6, the wearable electronic device 200 of FIG. 10, or the wearable electronic device 200 of FIG. 12) may include a housing 210, a processor 220, memory 230, a circuit board 440, 540, 640, 740, or 840, at least one light emitter 250, at least one sensor 260, a charging circuit 277, a battery 489, 589, 689, 789, or 889, a communication module 290, or an antenna 297.

The configuration of the housing 210, the processor 220, the memory 230, the circuit board 440, 540, 640, 740, or 840, the at least one light emitter 250, the at least one sensor 260, the charging circuit 277, the battery 489, 589, 689, 789, or 889, the communication module 290, or the antenna 297 of FIGS. 15 to 19 may be the same in whole or part as the configuration of the housing 210, the processor 220, the memory 230, the circuit board 240, the at least one light emitter 250, the at least one sensor 260, the charging circuit 277, the battery 289, the communication module 290, or the antenna 297 of FIG. 12.

According to an embodiment, the housing 210 may include an external housing portion 211 (e.g., the external housing portion 211 of FIG. 12) and an internal housing portion 213 (e.g., the internal housing portion 213 of FIG. 12) coupled to the external housing portion 211.

According to an embodiment, the processor 220, the memory 230, or the communication module 290 may be disposed and/or mounted on the circuit board 440, 540, 640, 740, or 840.

Referring to FIG. 15, the wearable electronic device 200 may include the battery 489. The battery 489 may be disposed in the housing 210.

According to an embodiment, the at least one light emitter 250 may include a first light emitter 451, a second light emitter 453, or a third light emitter 455. The first light emitter 451, the second light emitter 453, and/or the third light emitter 455 may be disposed and/or mounted on the circuit board 440. The first light emitter 451, the second light emitter 453, and/or the third light emitter 455 each may emit light of substantially the same wavelength or different wavelengths to measure the user's oxygen saturation to emit light to the user's body part (e.g., a finger, the skin of the finger, and/or a blood vessel). The first light emitter 451, the second light emitter 453, and/or the third light emitter 455 may be spaced apart from each other in the circumferential direction of the housing 210 inside the housing 210. Light emitted from the first light emitter 451, the second light emitter 453, and/or the third light emitter 455 may be reflected by or passed through the user's body part and may be received by the at least one sensor 260.

According to an embodiment, the at least one sensor 260 may include a first sensor 461, a second sensor 463, or a third sensor 465. The first sensor 461, the second sensor 463, and/or the third sensor 465 may be configured to receive at least a portion of light emitted from the at least one light emitter 250. The first sensor 461, the second sensor 463, and/or the third sensor 465 may be electrically connected to the circuit board 440. At least one of the first sensor 461, the second sensor 463, or the third sensor 465 may be disposed on the battery 489. For example, the second sensor 463 may be disposed on the battery 489. The first sensor 461 and/or the third sensor 465 may be disposed and/or mounted on the circuit board 440.

According to an embodiment, the processor 220 may obtain oxygen saturation information about the user using a signal (e.g., light) detected by the first sensor 461, the second sensor 463, and/or the third sensor 465.

According to an embodiment, the wearable electronic device 200 may include a temperature sensor 285. The temperature sensor 285 may be disposed and/or mounted on the circuit board 440. The temperature sensor 285 may be a sensor that measures the internal temperature of the wearable electronic device 200 or the user's body. It may be of a contact type or a non-contact type. The temperature value measured through the temperature sensor 285 may be stored in the memory 230 or may be transferred to the processor 220. The processor 220 may measure the body temperature of the user or the temperature of the wearable electronic device 200 using the temperature sensor 285.

According to an embodiment, the wearable electronic device 200 may include an inertial sensor 286. The inertial sensor 286 may be disposed and/or mounted on the circuit board 440. The inertial sensor 286 may be a sensor that detects inertia, such as an acceleration sensor or a gyroscope. The inertial sensor 286 may include only an acceleration sensor (e.g., a three-axis sensor), or may include an acceleration sensor and a gyroscope (e.g., a six-axis sensor). The processor 220 may sense a motion, gesture, impact, posture, or activity of the wearable electronic device 200 using the inertial sensor 286. For example, the processor 220 may include an acceleration sensor 286 disposed in the housing 210. The processor 220 may be configured to identify a change in the posture of the user using the acceleration sensor 286. The processor 220 may control the light emitter 250 to emit the first light based at least partially on identifying that the posture of the user has changed. The processor 220 may be configured to receive a first signal corresponding to the first light through the first sensor 261.

According to an embodiment, the wearable electronic device 200 may include a power management module 288. The power management module 288 may be disposed and/or mounted on the circuit board 440. The power management module 288 may be a module for managing the power of the wearable electronic device 200. The wearable electronic device 200 may distribute and control power appropriately to the processor 220, the at least one light emitter 250, or the at least one sensor 260 through the power management module 288.

According to an embodiment, the wearable electronic device 200 may include a controller 287 of the PPG sensor. The controller 287 of the PPG sensor may be disposed and/or mounted on the circuit board 440. The controller 287 of the PPG sensor may include an integrated circuit (IC) or an analog front end (AFE). The controller 287 of the PPG sensor may control the at least one light emitter 250 and/or the at least one sensor 260, process the received data, and transmit the data to the processor 220 or store the data in the memory 230.

Referring to FIG. 16, the wearable electronic device 200 may include a battery 589. The battery 589 may be disposed in the housing 210.

According to an embodiment, the wearable electronic device 200 may include a connection substrate 542. The connection substrate 542 may be disposed inside the housing 210. The connection substrate 542 may extend from the circuit board 540. The connection substrate 542 may be electrically connected to the circuit board 540. The connection substrate 542 may include a flexible printed circuit board (FPCB).

According to an embodiment, in order to measure the oxygen saturation of the user, the at least one light emitter 250 may emit light of substantially the same wavelength or each of different wavelengths, and may emit light to a body part (e.g., a finger, a skin of a finger, and/or a blood vessel) of the user. At least one light emitter 250 may be disposed and/or mounted on the circuit board 540. Light emitted from the at least one light emitter 250 may be reflected by or passed through the user's body part and received by the at least one sensor 260. For example, the light emitted from the at least one light emitter 250 may be passed through the user's body part along the first light path 51 and propagate to the first sensor 561, or may be reflected by the body part of the user along the second light path 53 and propagate to the second sensor 563. In case the user's body part is not inside the user's body (e.g., a finger), the first light path 51 includes a path through the user's body part, and the second light path 53 includes a path outside the user's body that is reflected by the user's body part. In case the user's body part is inside the user's body (e.g., a blood vessel of a finger), the first light path 51 includes a path inside the user's body that passes through the user's body part inside the user's body, and the second light path 53 includes a path inside the user's body that is reflected by the user's body part inside the user's body.

According to an embodiment, the at least one sensor 260 may include a first sensor 561 or a second sensor 563. The first sensor 561 and/or the second sensor 563 may be configured to receive light emitted from the at least one light emitter 250. The first sensor 561 and/or the second sensor 563 may be electrically connected to the circuit board 540. The first sensor 561 and/or the second sensor 563 may be disposed and/or mounted on the connection substrate 542.

According to an embodiment, the battery 589 may include a first recess 5891 or a second recess 5893. The first recess 5891 and/or the second recess 5893 may be recessed in the battery 589. The first sensor 561 may be disposed in the first recess 5891. The second sensor 563 may be disposed in the second recess 5893.

According to an embodiment, the processor 220 may obtain oxygen saturation information about the user using a signal (e.g., light) detected by the first sensor 561 and/or the second sensor 563.

Referring to FIG. 17, the wearable electronic device 200 may include a battery 689. The battery 689 may be disposed in the housing 210.

According to an embodiment, the wearable electronic device 200 may include a connection substrate 642. The connection substrate 642 may be disposed inside the housing 210. The connection substrate 642 may extend from the circuit board 640. The connection substrate 642 may be electrically connected to the circuit board 640. The connection substrate 542 may include a flexible printed circuit board (FPCB).

According to an embodiment, in order to measure the oxygen saturation of the user, the at least one light emitter 250 may emit light of substantially the same wavelength or each of different wavelengths, and may emit light to a body part (e.g., a finger, a skin of a finger, and/or a blood vessel) of the user. At least one light emitter 250 may be disposed and/or mounted on the circuit board 640. Light emitted from the at least one light emitter 250 may be reflected by or passed through the user's body part and received by the at least one sensor 260. For example, the light emitted from the at least one light emitter 250 may be passed through the user's body part along the first light path 61 and propagate to the first sensor 661, or may be reflected by the body part of the user along the second light path 63 and propagate to the second sensor 663. In case the user's body part is not inside the user's body (e.g., a finger), the first light path 61 includes a path through the user's body part, and the second light path 63 includes a path outside the user's body that is reflected by the user's body part. In case the user's body part is inside the user's body (e.g., a blood vessel of a finger), the first light path 61 includes a path inside the user's body that passes through the user's body part inside the user's body, and the second light path 63 includes a path inside the user's body that is reflected by the user's body part inside the user's body.

According to an embodiment, the at least one sensor 260 may include a first sensor 661 or a second sensor 663. The first sensor 661 and/or the second sensor 663 may be configured to receive light emitted from the at least one light emitter 250. The first sensor 661 and/or the second sensor 663 may be electrically connected to the circuit board 640. The first sensor 661 and/or the second sensor 663 may be disposed and/or mounted on the connection substrate 642.

According to an embodiment, the first sensor 661 and/or the second sensor 663 may not be positioned in the inner space of the wearable electronic device 200 formed by the external housing portion 211 and the internal housing portion 213. For example, the first sensor 661 and/or the second sensor 663 may be positioned to protrude from the internal housing portion 213 toward the center O of the wearable electronic device.

According to an embodiment, the housing 210 may include a cover housing portion 215. The cover housing portion 215 may be coupled to the internal housing portion 213. The cover housing portion 215 may be configured to cover at least one sensor 260. The cover housing portion 215 may include a transparent material (e.g., resin) through which light may be transmitted. The cover housing portion 215 may include a first cover housing portion 2151 or a second cover housing portion 2153. The first cover housing portion 2151 may be configured to cover the first sensor 661. The second cover housing portion 2153 may be configured to cover the second sensor 663.

According to an embodiment, the processor 220 may obtain oxygen saturation information about the user using a signal (e.g., light) detected by the first sensor 661 and/or the second sensor 663.

Referring to FIG. 18, the wearable electronic device 200 may include a battery 789. The battery 789 may be disposed in the housing 210.

According to an embodiment, the wearable electronic device 200 may include a connection substrate 742. The connection substrate 742 may be disposed inside the housing 210. The connection substrate 742 may extend from the circuit board 740. The connection substrate 742 may be electrically connected to the circuit board 740. The connection substrate 742 may include a flexible printed circuit board (FPCB).

According to an embodiment, the at least one light emitter 250 may include a first light emitter 751, a second light emitter 753, or a third light emitter 755. The first light emitter 751 may be disposed on the circuit board 740. The second light emitter 753 and/or the third light emitter 755 may be disposed and/or mounted on the connection substrate 742. The first light emitter 751, the second light emitter 753, and/or the third light emitter 755 each may emit light of substantially the same wavelength or different wavelengths to measure the user's oxygen saturation to emit light to the user's body part (e.g., a finger, the skin of the finger, and/or a blood vessel). The first light emitter 751, the second light emitter 753, and/or the third light emitter 755 may be spaced apart from each other in the circumferential direction of the housing 210 inside the housing 210. Light emitted from the first light emitter 751, the second light emitter 753, and/or the third light emitter 755 may be reflected by or passed through the user's body part and may be received by the at least one sensor 260.

According to an embodiment, the at least one sensor 260 may include a first sensor 761 or a second sensor 763. The first sensor 761 and/or the second sensor 763 may be configured to receive light emitted from the at least one light emitter 250. The first sensor 761 and/or the second sensor 763 may be electrically connected to the circuit board 740. The first sensor 761, the second sensor 763, and/or the third sensor 765 may be disposed and/or mounted on the connection substrate 742.

According to an embodiment, the second light emitter 753, the third light emitter 755, the first sensor 761, the second sensor 763, and/or the third sensor 765 may not be positioned in the inner space of the wearable electronic device 200 formed by the external housing portion 211 and the internal housing portion 213. For example, the second light emitter 753, the third light emitter 755, the first sensor 761, the second sensor 763, and/or the third sensor 765 may be positioned to protrude from the internal housing portion 213 toward the center O of the wearable electronic device.

According to an embodiment, the housing 210 may include a cover housing portion 215. The cover housing portion 215 may be coupled to the internal housing portion 213. The cover housing portion 215 may be configured to cover the second light emitter 753, the third light emitter 755, the first sensor 761, the second sensor 763, and/or the third sensor 765. The cover housing portion 215 may include a transparent material (e.g., resin) through which light may be transmitted. The cover housing portion 215 may include a first cover housing portion 3151, a second cover housing portion 3152, a third cover housing portion 3153, a fourth cover housing portion 3154, or a fifth cover housing portion 3155. The first cover housing portion 3151 may be configured to cover the first sensor 761. The second cover housing portion 3153 may be configured to cover the second light emitter 753. The third cover housing portion 3153 may be configured to cover the second sensor 763. The fourth cover housing portion 3154 may be configured to cover the third light emitter 755. The fifth cover housing portion 3155 may be configured to cover the third sensor 765.

According to an embodiment, the processor 220 may obtain oxygen saturation information about the user using a signal (e.g., light) detected by the first sensor 761, the second sensor 763, and/or the third sensor 765.

Referring to FIG. 19, the wearable electronic device 200 may include the battery 889. The battery 889 may be disposed in the housing 210.

According to an embodiment, the wearable electronic device 200 may include a connection substrate 842. The connection substrate 842 may be disposed inside the housing 210. The connection substrate 842 may extend from the circuit board 840. The connection substrate 842 may be electrically connected to the circuit board 840. The connection substrate 842 may include a flexible printed circuit board (FPCB).

According to an embodiment, the at least one light emitter 250 may include a first light emitter 851 or a second light emitter 853. The first light emitter 851 and/or the second light emitter 853 may be disposed and/or mounted on the connection substrate 842. The first light emitter 851 and/or the second light emitter 853 each may emit light of substantially the same wavelength or different wavelengths to measure the user's oxygen saturation to emit light to the user's body part (e.g., a finger, the skin of the finger, and/or a blood vessel). The first light emitter 851 and/or the second light emitter 853 may be spaced apart from each other in the circumferential direction of the housing 210 inside the housing 210. Light emitted from the first light emitter 851 and/or the second light emitter 853 may be reflected by or passed through the user's body part and may be received by the at least one sensor 260.

According to an embodiment, the light emitted from the first light emitter 851 may be passed through the user's body part along the first light path 81 and propagate to the at least one sensor 260. The light emitted from the second light emitter 853 may be reflected by the user's body part along the second light path 83 and propagate to the at least one sensor 260. In case the user's body part is not inside the user's body (e.g., a finger), the first light path 81 includes a path through the user's body part, and the second light path 83 includes a path outside the user's body that is reflected by the user's body part. In case the user's body part is inside the user's body (e.g., a blood vessel of a finger), the first light path 81 includes a path inside the user's body that passes through the user's body part inside the user's body, and the second light path 83 includes a path inside the user's body that is reflected by the user's body part inside the user's body.

According to an embodiment, the at least one sensor 260 may be configured to receive light emitted from the at least one light emitter 250. At least one sensor 260 may be disposed and/or mounted on the circuit board 840.

According to an embodiment, the processor 220 may obtain oxygen saturation information about the user using a signal (e.g., light) detected by the at least one sensor 260.

As users' interest in health increases, technologies for measuring biometric signals through wearable electronic devices carried by users are being developed. For example, it is possible to measure heart rate, electrocardiogram, blood pressure, pulse rate, respiratory rate, body temperature, and oxygen saturation (SpO2) through a sensor included in the electronic device.

A sensor may be disposed in the wearable electronic device to acquire biometric information about the user's heart rate or blood oxygen saturation. As an example, the photoplethysmography (PPG) sensor may include a light source and a light receiving unit for receiving light emitted from the light source, and the wearable electronic device may acquire biometric information about the user based on an optical signal detected by the light receiving unit.

In the case of a ring-type wearable electronic device worn on the user's finger, the obtained biometric information may be provided as inaccurate information as the optical signal detected by the light receiving unit deteriorates according to the user's sleeping posture or a thick blood vessel is positioned on the path of the light.

Meanwhile, the light emitted from the light source is passed through or reflected by the blood vessels or skin of the user. In general, it is known that the biometric information about the user is more accurate when the biometric information about the user is obtained based on the optical signal passed through the finger of the user. However, there is a problem that there is significant current consumption to emit the light passed through the finger of the user. Further, when the biometric information about the user is obtained based on the optical signal reflected by the finger of the user, it is known that the current consumption is relatively low, but there is a problem that the accuracy of the biometric information is low.

According to an embodiment of the disclosure, there may be provided a wearable electronic device capable of obtaining the user's biometric information based on light reflected by or passed through the user's finger through a plurality of sensors.

According to an embodiment of the disclosure, there may be provided a wearable electronic device capable of increasing the reliability of oxygen saturation obtained through a reflective sensor using a transmissive sensor when detecting the user's oxygen saturation using the reflective sensor.

The disclosure is not limited to the foregoing embodiments but various modifications or changes may rather be made thereto without departing from the spirit and scope of the disclosure.

According to an embodiment of the disclosure, it is possible to reduce the current consumption of the wearable electronic device by minimizing the operation time of the transmissive sensor which has high accuracy.

According to an embodiment of the disclosure, the wearable electronic device may provide more reliable biometric information by identifying the accuracy of biometric information or calibrating the biometric information based on the signal detected by the reflective sensor through the transmissive sensor having higher accuracy.

Effects obtainable from the disclosure are not limited to the above-mentioned effects, and other effects not mentioned may be apparent to one of ordinary skill in the art from the following description.

According to an embodiment of the disclosure, a wearable electronic device 200 may comprise a housing 210, a light emitter 250, a first sensor 261, a second sensor 263, at least one processor 220, or memory 230. The housing 210 may include an external housing portion 211 or an internal housing portion 213. The internal housing portion 213 may be coupled to the external housing portion 211. The internal housing portion 213 may be configured to be at least partially transparent. The light emitter 250 may be disposed in the housing 210. The light emitter 250 may be configured to emit light through the internal housing portion 213. The first sensor 261 may be disposed in the housing 210. The first sensor 261 may be configured to receive light passed through a user's finger. The second sensor 263 may be disposed in the housing 210. The second sensor 263 may be configured to receive light reflected by the user's finger. The at least one processor may include a processing circuitry. The memory 230 may store instructions. The instructions may, when executed individually or collectively by the at least one processor 220, cause the wearable electronic device 200 to control the light emitter 250 to emit first light, receive, via the first sensor 261, a first signal corresponding to the first light, control the light emitter 250 to emit second light, receive, via the second sensor 263, a second signal corresponding to the second light, and generate biometric information based on the first signal or the second signal.

According to an embodiment, the biometric information may include information on oxygen saturation or information on heart rate.

According to an embodiment, the light emitter 250 may be configured to emit light of a plurality of wavelength bands including a red wavelength and an infrared wavelength.

According to an embodiment, a distance between the first sensor 261 and the light emitter 250 may be greater than a distance between the second sensor 263 and the light emitter 250.

According to an embodiment, the instructions may, when executed individually or collectively by the at least one processor 220, cause the wearable electronic device 200 to control the light emitter 250 to emit the second light having a first intensity, and control the light emitter 250 to emit the first light having a second intensity different from the first intensity after the second light is emitted.

According to an embodiment, the first intensity may be smaller than the second intensity.

According to an embodiment, the instructions may, when executed individually or collectively by the at least one processor 220, cause the wearable electronic device 200 to: based at least in part on identification that a difference between the first signal and the second signal is less than or equal to a threshold value, generate the biometric information using the second signal.

According to an embodiment, the instructions may, when executed individually or collectively by the at least one processor 220, cause the wearable electronic device 200 to: based at least in part on identification that the difference between the first signal and the second signal is more than a threshold value, generate the biometric information by calibrating the second signal.

According to an embodiment, the instructions may, when executed individually or collectively by the at least one processor 220, cause the wearable electronic device 200 to: adjust a light emission intensity or a light emission period of the light emitter 250, based at least in part on the difference.

According to an embodiment, the instructions may, when executed individually or collectively by the at least one processor 220, cause the wearable electronic device 200 to: generate the biometric information by adding a calibration value corresponding to the difference to the second signal.

According to an embodiment, the wearable electronic device 200 may further comprise an acceleration sensor 286. The acceleration sensor 286 may be disposed in the housing 210. The instructions may, when executed individually or collectively by the at least one processor 220, cause the wearable electronic device 200 to: identify a change in a posture of the user using the acceleration sensor 286, based at least in part on identification that the posture of the user is changed, control the light emitter 250 to emit the first light, and receive, via the first sensor (261), the first signal corresponding to the first light.

According to an embodiment, the wearable electronic device 200 may further comprise a third sensor 265. The third sensor 265 may be disposed in the housing 210. The third sensor 265 may be positioned between the first sensor 261 and the second sensor 263. The third sensor 265 may be configured to receive light reflected by the user's finger. The instructions may, when executed individually or collectively by the at least one processor 220, cause the wearable electronic device 200 to: receive, via the third sensor 265, a third signal corresponding to third light and based at least in part on identification that a difference between the first signal and the third signal is less than a difference between the first signal and the second signal, generate the biometric information.

According to an embodiment, the wearable electronic device 200 may further comprise a first wall 271, a second wall 273, or a battery 289. The first wall 271 may be positioned between the first sensor 261 and the second sensor 263. The second wall 273 may be positioned between the second sensor 263 and the light emitter 250. The battery 289 may be disposed in the housing 210.

According to an embodiment, at least one of the light emitter 250, the first sensor 461, or the second sensor 463 may be disposed on the battery 489.

According to an embodiment of the disclosure, a wearable electronic device 200 may comprise a housing 210, a light emitter 250, a first sensor 261, a second sensor 263, at least one processor 220, or memory 230. The housing 210 may include an external housing portion 211 or an internal housing portion 213. The internal housing portion 213 may be coupled to the external housing portion 211. The internal housing portion 213 may be configured to be at least partially transparent. The light emitter 250 may be disposed in the housing 210. The light emitter 250 may be configured to emit light through the internal housing portion 213. The first sensor 261 may be disposed in the housing 210. The first sensor 261 may be configured to receive light passed through a user's finger. The second sensor 263 may be disposed in the housing 210. The second sensor 263 may be configured to receive light reflected by the user's finger. The at least one processor 220 may include a processing circuitry. The memory 230 may store instructions. The instructions may, when executed individually or collectively by the at least one processor 220, cause the wearable electronic device 200 to: control the light emitter 250 to emit first light, receive, via the first sensor 261, a first signal, control the light emitter 250 to emit second light, receive, via the second sensor 263, a second signal, based at least in part on identification that a difference between the first signal and the second signal is less than or equal to a threshold value, generate biometric information, and based at least in part on identification that the difference between the first signal and the second signal is more than the threshold value, generate the biometric information by calibrating the second signal with a calibration value corresponding to the difference.

According to an embodiment, the biometric information may include information on oxygen saturation or information on heart rate.

According to an embodiment, the wearable electronic device 200 may further comprise an acceleration sensor 286. The acceleration sensor 286 may be disposed in the housing 210. The instructions may, when executed by the at least one processor 220, cause the wearable electronic device 200 to: identify a change in a posture of the user using the acceleration sensor 286, based at least in part identification that the posture of the user is changed, control the light emitter 250 to emit the first light, and receive, via the first sensor 261, the first signal corresponding to the first light.

According to an embodiment of the disclosure, a housing 210, a first sensor 261, a second sensor 263, a third sensor 265, at least one processor 220, or memory 230 may be included. The housing 210 may have a ring shape. The housing 210 may include an external housing portion 211 or an internal housing portion 213. The internal housing portion 213 may be coupled to the external housing portion 211. The internal housing portion 213 may be configured to be at least partially transparent. The light emitter 250 may be disposed in the housing 210. The light emitter 250 may be configured to emit light through the internal housing portion 213. The light emitter 250 may be disposed in the housing 210. The light emitter 250 may be configured to receive light passed through a user's finger. The second sensor 263 may be disposed in the housing 210. The second sensor 263 may be configured to receive light reflected by the user's finger. The third sensor 265 may be disposed in the housing 210. The third sensor 265 may be positioned between the first sensor 261 and the second sensor 263. The third sensor 265 may be configured to receive light reflected by the user's finger. The at least one processor 220 may include a processing circuitry. The memory 230 may store instructions. The instructions may, when individually or collectively executed by the at least one processor 220, cause the wearable electronic device 200 to: generate information on oxygen saturation using a signal received through the first sensor 261, a signal received through the second sensor 263, and a signal received through the third sensor 265.

According to an embodiment, the instructions may, when individually or collectively executed by the at least one processor 220, cause the wearable electronic device 200 to: control the light emitter 250 to emit light of a first intensity for detecting light in the second sensor 263, control the light emitter 250 to emit light of a second intensity for detecting light in the third sensor 265, and control the light emitter 250 to emit light of a third intensity for detecting light in the first sensor 261. The first intensity, the second intensity, and the third intensity may differ from each other.

According to an embodiment, the wearable electronic device 200 may further comprise a battery 289. The battery 289 may be disposed in the housing 210. The battery 289 may have a at least partially bent shape.

The electronic device according to various embodiments of the disclosure may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The storage medium readable by the machine may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. Some of the plurality of entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A ring-type wearable electronic device comprising:
   a ring-shape housing including a first housing portion and a second housing portion coupled to the first housing portion, wherein the second housing portion is configured to contact a finger of a user wearing the ring-type wearable electronic device;
   a first light source including a plurality of light emitters disposed in the ring-shape housing, and configured to emit light of red wavelength and infrared wavelength bands towards the finger;
   a first sensor disposed in the ring-shape housing, and configured to receive light emitted by the first light source;
   a second sensor disposed in the ring-shape housing, and configured to receive light emitted by the first light source, wherein the first sensor is positioned farther from the first light source than the second sensor is position from the first light source;
   a flexible printed circuit board (FPCB) disposed in the ring-shape housing, wherein the first light source, the first sensor, and the second sensor are disposed on the FPCB at least partially bent corresponding to the ring-shape housing;
   at least one processor including a processing circuitry; and
   memory storing instructions,
   wherein the instructions, when executed by the at least one processor individually or collectively, cause the ring-type wearable electronic device to:
      emit, by the first light source at a first time, first light of red wavelength and infrared wavelength bands, the first light being configured to reach the first sensor through the finger,
      based on the first light emitted by the first light source at the first time, obtain first information corresponding to part of the first light that is received by the first sensor via the finger,
      emit, by the first light source at a second time different from the first time, second light of red wavelength and infrared wavelength bands, the second light being configured to reach the second sensor through the finger,
      based on the second light emitted by the first light source at the second time, obtain second information corresponding to part of the second light that is received by the second sensor via the finger, and
      acquire an oxygen saturation information of the user based on at least one of the first information or the second information, and
   wherein a first angle formed by the first light source and the second sensor with respect to a center of the ring-type wearable electronic device is smaller than a second angle formed by the first light source and the first sensor with respect to the center of the ring-type wearable electronic device.

2. The ring-type wearable electronic device of claim 1,
   wherein the part of the first light that is received by the first sensor via the finger propagates via a first light path through the finger, and
   wherein the part of the second light that is received by the second sensor via the finger propagates via a second light path, different than the first light path, through the finger.

3. The ring-type wearable electronic device of claim 1, further comprising:
   a battery disposed in the ring-shape housing and at least partially bent corresponding to the ring-shape housing.

4. The ring-type wearable electronic device of claim 1, wherein the first light has a first intensity and the second light has a second intensity lower than the first intensity.

5. The ring-type wearable electronic device of claim 1,
   wherein the first housing portion includes a titanium material, and the second housing portion includes a titanium material, and
   wherein part of the second housing portion includes a material through which the light passes.

6. The ring-type wearable electronic device of claim 1, further comprising:
   a second light source disposed in the ring-shape housing and between the first sensor and the second sensor along the ring-shape housing, and configured to emit light of red wavelength and infrared wavelength bands towards the finger, wherein the second light source is positioned closer to the first sensor than the second light source is positioned to the second sensor.

7. The ring-type wearable electronic device of claim 6, wherein the instructions, when executed by the at least one processor individually or collectively, cause the ring-type wearable electronic device to:

emit, by the second light source, third light of red wavelength and infrared wavelength bands, the third light being configured to reach the first sensor through the finger.

8. The ring-type wearable electronic device of claim 6, wherein the instructions, when executed by the at least one processor individually or collectively, cause the ring-type wearable electronic device to:

emit, by the second light source, fourth light of red wavelength and infrared wavelength bands, the fourth light being configured to reach the second sensor through the finger.

9. The ring-type wearable electronic device of claim 7, wherein the instructions, when executed by the at least one processor individually or collectively, cause the ring-type wearable electronic device to:

emit, by the second light source, fourth light of red wavelength and an infrared wavelength bands, the fourth light being configured to reach the second sensor through the finger.

10. A ring-type wearable electronic device comprising:
a ring-shape housing including a first housing portion and a second housing portion coupled to the first housing portion, wherein the second housing portion is configured to contact a finger of a user wearing the ring-type wearable electronic device;
a first light source including a plurality of light emitters disposed in an ring-shape housing, and configured to emit light of red wavelength and infrared wavelength bands;
a first sensor disposed in the ring-shape housing, and configured to receive light emitted by the first light source;
a second sensor disposed in the ring-shape housing, and configured to receive light emitted by the first light source, wherein the first sensor is positioned farther from the first light source than the second sensor is position from the first light source;
a second light source disposed in the ring-shape housing and between the first sensor and the second sensor along the ring-shape housing, and configured to emit light of red wavelength and infrared wavelength bands towards the finger, wherein the second light source is positioned closer to the first sensor than the second sensor is positioned to the second sensor;
at least one processor including a processing circuitry; and
memory storing instructions,
wherein the instructions, when executed by the at least one processor individually or collectively, cause the ring-type wearable electronic device to:
emit, by the first light source, first light of red wavelength and infrared wavelength bands, the first light being configured to reach the first sensor through the finger,
based on the first light emitted by the first light source, obtain first information corresponding to part of the first light that is received by the first sensor via the finger, emit, by the first light source, second light of red wavelength and infrared wavelength bands, the second light being configured to reach the second sensor through the finger,
based on the second light emitted by the first light source, obtain second information corresponding to part of the second light that is received by the second sensor via the finger, and
acquire an oxygen saturation of the user based on at least one of the first information or the second information, and
wherein a first angle formed by the first light source and the second sensor with respect to a center of the ring-type wearable electronic device is smaller than a second angle formed by the first light source and the first sensor with respect to the center of the ring-type wearable electronic device.

11. The ring-type wearable electronic device of claim 10, wherein the instructions, when executed by the at least one processor individually or collectively, cause the ring-type wearable electronic device to:

emit, by the second light source, third light of red wavelength and infrared wavelength bands, the third light being configured to reach the first sensor through the finger.

12. The ring-type wearable electronic device of claim 10, wherein the instructions, when executed by the at least one processor individually or collectively, cause the ring-type wearable electronic device to:

emit, by the second light source, fourth light of red wavelength and infrared wavelength bands, the fourth light being configured to reach the second sensor through the finger.

13. The ring-type wearable electronic device of claim 11, wherein the instructions, when executed by the at least one processor individually or collectively, cause the ring-type wearable electronic device to:

emit, by the second light source, fourth light of red wavelength and infrared wavelength bands, the fourth light being configured to reach the second sensor through the finger.

14. The ring-type wearable electronic device of claim 10, further comprising:
a flexible printed circuit board (FPCB) disposed in the ring-shape housing and at least partially bent corresponding to the ring-shape housing,
wherein the first light source, the second light source, the first sensor, and the second sensor are disposed on the FPCB.

15. The ring-type wearable electronic device of claim 10, further comprising:
a battery disposed in the ring-shape housing and at least partially bent corresponding to the ring-shape housing.

16. The ring-type wearable electronic device of claim 10, wherein the first light has a first intensity and the second light has a second intensity lower than the first intensity.

17. The ring-type wearable electronic device of claim 10, wherein the first housing portion includes a titanium material, and the second housing portion includes a titanium material, and
wherein part of the second housing portion includes a material through which the light passes.

18. The ring-type wearable electronic device of claim 10, wherein the first light and the second light are emitted at different time points.

19. A ring-type wearable electronic device comprising:
a ring-shape housing including a first housing portion and a second housing portion coupled to the first housing portion, wherein the second housing portion is configured to contact a finger of a user wearing the ring-type wearable electronic device;
a first light source including a plurality of light emitters disposed in the ring-shape housing, and configured to emit light of red wavelength and infrared wavelength bands towards the finger;
a first sensor disposed in the ring-shape housing, and configured to receive light emitted by the first light source;
a second sensor disposed in the ring-shape housing, and configured to receive light emitted by the first light source, wherein the first sensor is positioned farther from the first light source than the second sensor is position from the first light source;
at least one processor including a processing circuitry; and
memory storing instructions,
wherein the instructions, when executed by the at least one processor individually or collectively, cause the ring-type wearable electronic device to:
  emit, by the first light source, first light, having a first intensity, of red wavelength and infrared wavelength bands, the first light being configured to reach the first sensor through the finger,
  based on the first light emitted by the first light source, obtain first information corresponding to part of the first light that is received by the first sensor via the finger,
  emit, by the first light source, second light, having a second intensity lower than the first intensity, of red wavelength and infrared wavelength bands, the second light being configured to reach the second sensor through the finger,
  based on the second light emitted by the first light source, obtain second information corresponding to part of the second light that is received by the second sensor via the finger, and
  acquire an oxygen saturation information of the user based on at least one of the first information or the second information, and
wherein a first angle formed by the first light source and the second sensor with respect to a center of the ring-type wearable electronic device is smaller than a second angle formed by the first light source and the first sensor with respect to the center of the ring-type wearable electronic device.

20. The ring-type wearable electronic device of claim 19, further comprising:
a flexible printed circuit board (FPCB) disposed in the ring-shape housing and at least partially bent corresponding to the ring-shape housing,
wherein the first light source, the first sensor, and the second sensor are disposed on the FPCB.

21. The ring-type wearable electronic device of claim 19, further comprising:
a battery disposed in the ring-shape housing and at least partially bent corresponding to the ring-shape housing.

22. The ring-type wearable electronic device of claim 19, wherein the first housing portion includes a titanium material, and the second housing portion includes a titanium material, and
wherein part of the second housing portion includes a material through which the light passes.

23. The ring-type wearable electronic device of claim 19, wherein the first light and the second light are emitted at different time points.

24. The ring-type wearable electronic device of claim 19, further comprising:
a second light source disposed in the ring-shape housing and between the first sensor and the second sensor along the ring-shape housing and configured to emit light of red wavelength and infrared wavelength bands,
wherein the second light source is positioned closer to the first sensor than the second sensor is positioned to the second sensor.

25. The ring-type wearable electronic device of claim 24, wherein the instructions, when executed by the at least one processor individually or collectively, cause the ring-type wearable electronic device to:
emit, by the second light source, third light of red wavelength and infrared wavelength bands, the third light being configured to reach the first sensor through the finger.

26. The ring-type wearable electronic device of claim 24, wherein the instructions, when executed by the at least one processor individually or collectively, cause the ring-type wearable electronic device to:
emit, by the second light source, fourth light of red wavelength and infrared wavelength bands, the fourth light being configured to reach the second sensor through the finger.

27. The ring-type wearable electronic device of claim 25, wherein the instructions, when executed by the at least one processor individually or collectively, cause the ring-type wearable electronic device to:
emit, by the second light source, fourth light of red wavelength and infrared wavelength bands, the fourth light being configured to reach the second sensor through the finger.

* * * * *